United States Patent [19]

Iwao et al.

[11] Patent Number: 4,584,300
[45] Date of Patent: Apr. 22, 1986

[54] PLATELET ANTI-AGGREGATIVE- AND CALCIUM ANTAGONISTIC -1,4-BENZOTHIAZIN-3-ONE DERIVATIVES, COMPOSITIONS, AND METHODS OF USE THEREFOR

[75] Inventors: Jun-ichi Iwao, Takarazuka; Tadashi Iso, Sakai; Masayuki Oya, Ibaraki, all of Japan

[73] Assignee: Santen Pharmaceutical Co., Ltd., Osaka, Japan

[21] Appl. No.: 571,467

[22] Filed: Jan. 17, 1984

[30] Foreign Application Priority Data

Feb. 7, 1983 [JP] Japan .................................. 58-19467
Feb. 9, 1983 [JP] Japan .................................. 58-20990

[51] Int. Cl.[4] ..................... A61K 31/54; C07D 279/16; C07D 417/12
[52] U.S. Cl. ........................................ 514/225; 544/52
[58] Field of Search ................... 544/58.2, 58.6, 58.7, 544/52; 424/246; 514/225

[56] References Cited

U.S. PATENT DOCUMENTS 3,166,554  1/1965  Krapcho ............................... 544/52
3,555,155  1/1971  Stearns ................................. 544/52

Primary Examiner—Henry R. Jiles
Assistant Examiner—J. G. Mullins
Attorney, Agent, or Firm—Frishauf, Holtz, Goodman & Woodward

[57] ABSTRACT

This invention relates to benzothiazine derivatives represented by the formula [I] and salts thereof, which are useful for treatment of cardiovascular diseases.

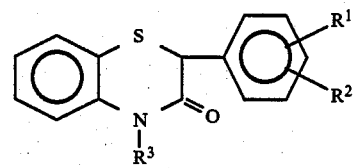

32 Claims, No Drawings

PLATELET ANTI-AGGREGATIVE- AND CALCIUM ANTAGONISTIC -1,4-BENZOTHIAZIN-3-ONE DERIVATIVES, COMPOSITIONS, AND METHODS OF USE THEREFOR

DETAILED DESCRIPTION OF THE INVENTION

This invention relates to novel benzothiazine derivatives of the formula [I] and salts thereof,

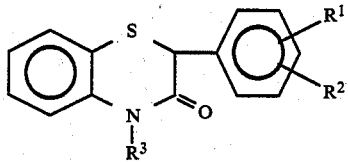

wherein
$R^1$ is selected from the group consisting of hydrogen, hydroxy, $(C_1-C_6)$alkoxy, $(C_1-C_6)$alkanoyloxy, $(C_1-C_6)$alkoxycarbonyloxy, tetrahydropyranyloxy, amino, $(C_1-C_6)$alkylamino and

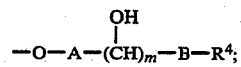

$R^2$ is selected from the group consisting of hydrogen, $(C_1-C_6)$alkyl, halogen, nitro, hydroxy, amino, $(C_1-C_6)$alkoxy, $(C_1-C_6)$alkanoyloxy, $(C_1-C_6)$alkylamino and $(C_1-C_6)$alkoxycarbonyloxy;
$R^3$ is hydrogen, $(C_1-C_6)$alkyl or

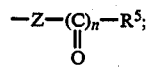

$R^4$ and $R^5$ are same or different and are selected from the group consisting of hydroxy, halogen, methoxy,

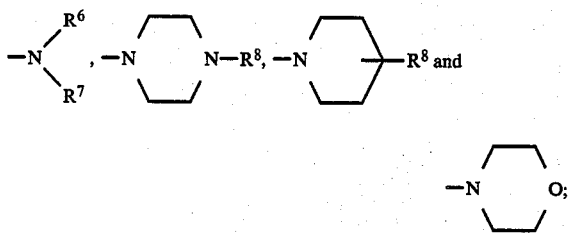

$R^6$ and $R^7$ are same or different and are selected from the group consisting of hydrogen, $(C_1-C_6)$alkyl, $(C_4-C_7)$cycloalkyl and phenyl-$(C_1-C_6)$ alkyl, and said phenyl nucleus can be substituted by hydroxy, $(C_1-C_6)$alkyl or $(C_1-C_6)$alkoxy;
$R^8$ is selected from the group consisting of hydrogen, $(C_1-C_6)$alkyl, $(C_1-C_6)$alkanoyl, $(C_1-C_6)$alkoxycarbonyl, carboxy, phenyl, phenylcarbonyl, phenyl-$(C_1-C_6)$alkyl, phenyl-$(C_1-C_6)$alkanoyl, and phenylcarbonyl-$(C_1-C_6)$alkyl, and said alkyl and alkanoyl groups can be substituted by hydroxy, $(C_1-C_6)$alkoxy, carboxy, $(C_1-C_6)$alkoxycarbonyl, halogen, amino, $(C_1-C_6)$alkylamino or tetrahydropyranyloxy, and said phenyl nucleus can be substituted by $(C_1-C_6)$alkyl, hydroxy, $(C_1-C_6)$alkoxy, $(C_1-C_6)$alkanoyl, $(C_1-C_6)$alkoxycarbonyl, halogen, amino or $(C_1-C_6)$alkylamino;
A, B and Z are same or different and are $(C_1-C_6)$alkylene; and
m and n each is 0 or 1,
when $R^3$ is hydrogen or n is 0, $R^1$ represents

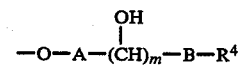

or hydroxy.

The compounds of this invention are novel benzothiazine derivatives. Main structure of the compounds is 3-oxo-1,4-benzothiazine wherein the 2-position of benzothiazine ring is substituted by substituted phenyl group.

2-Phenyl-3-oxo-1,4-benzothiazine derivatives are reported by J. Krapcho (U.S. Pat. No. 3,166,554 and Brit. Patent No. 960,612), Stearns et al. (U.S. Pat. No. 3,555,155) and Stanley O. et al. (Canadian Patent No. 717,979).

The U.S. Pat. and Brit. Pat. of J. Krapcho relate to 2-phenyl-3-oxo-1,4-benzothiazine in which phenyl nucleus is unsubstituted or substituted by halogen, and the pharmacological effect is for the treatment of Parkinsonism.

The U.S. Pat. of Stearns et al. relates to 2-(alkoxyphenyl)benzothiazine derivatives and the pharmacological effect is for the control of insects.

The Can. Pat. of Stanley et al. relates to 2-(unsubstitutedphenyl)benzothiazine derivatives and the pharmacological effects are for anticholinergic and antihistaminic.

The compounds of this invention are not only new in chemical structure but also found useful for treatment of cardiovascular diseases and such effect on cardiovascular diseases has not been found in the known 2-phenyl-3-oxo-1,4-benzothiazine derivatives.

Cardiovascular diseases are angina cordis, arrhythmia, thrombosis, etc., and β-blocker, inhibitor of platelet aggregation, calcium antagonist, etc., are used as therapeutic agent.

From the pharmacological tests, it is proved that the compounds of this invention possess superior platelet antiaggregation effect and calcium antagonistic effect, so they are useful for cardiovascular diseases.

Processes for preparing the compounds of this invention are summarized as follows and explained in detail by working examples.

First step is shown by the following schema.

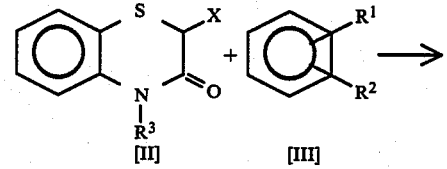

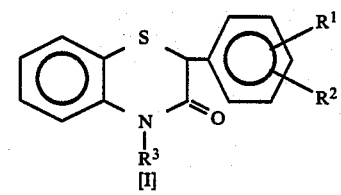

wherein X is halogen or methanesulfonyloxy.

This reaction is Friedel-Crafts like reaction, which is performed without specific catalyst, but if necessary, using Lewis acid such as AlCl₃ as catalyst.

According to the varieties of the substituents, the following reactions [(1)–(3)] may be followed. (1) First case: R¹ in the formula [I] is hydroxy (represented by the formula [IV]).

The compound [IV] is reacted with halide of the formula [V] to produce the compound of the formula [VI],

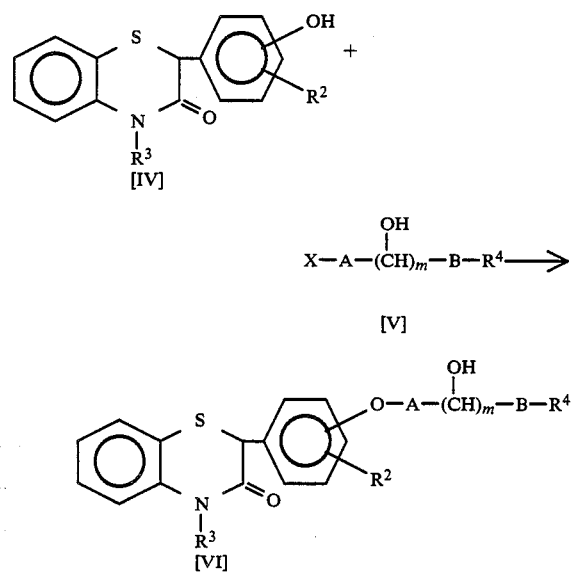

wherein —OH group and R⁴ may be joined to form epoxy ring.

This reaction is performed in the presence of base such as sodium hydride, sodium ethoxide, sodium hydroxide, etc.

(1)-(a) When R⁴ in the formula [VI] represents halogen (formula [VII]), if necessary, the compound is reacted with amine derivative of the formula [VIII] to produce the compound of the formula [IX],

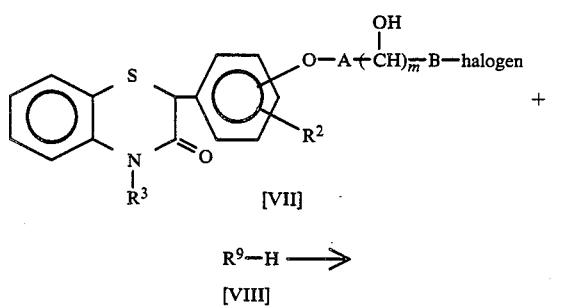

wherein R⁹ is

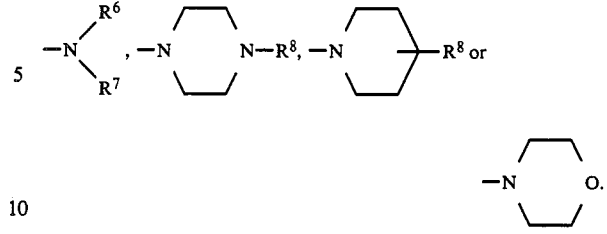

This reaction is performed with or without base (sodium carbonate, potassium hydroxide, triethylamine, etc.) in organic solvent (benzene, ethanol, dimethylformamide, etc.) or without solvent, and, if necessary, in the presence of catalyst such as sodium iodide.

(2) Second case: R³ in the formula [I] is hydrogen (represented by the formula [X]).

The compound of the formula [X] is reacted with halide of the formula [XI] to produce the compound of the formula [XII].

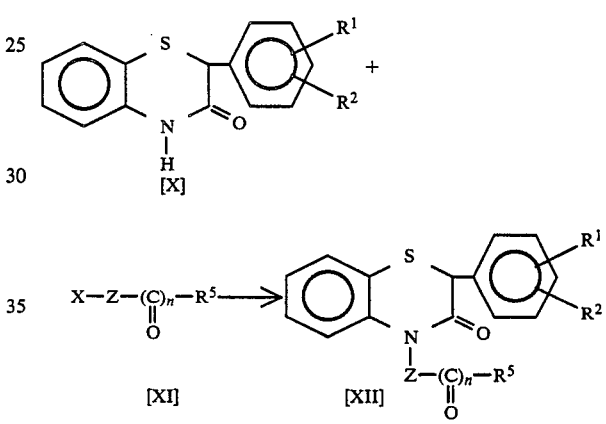

This reaction is performed in the presence of base such as sodium hydride, sodium ethoxide, sodium hydroxide, etc.

(2)-(a) When R⁵ in the formula [XII] is hydroxy, if necessary, the compound [XII] is esterified by diazoalkane (diazomethane, etc.), alkyl halide and base, or alcohol and acid. If R¹ and/or R² in the formula [XII] are/is hydroxy, the hydroxy group(s) may be converted to alkoxy group(s) in the esterification step. Said ester in which R¹ and/or R² are/is converted to alkoxy, if necessary, is hydrolized with base.

(2)-(b) When R⁵ in the formula [XII] is hydroxy (represented by the formula [XIII]), if necessary, the compound [XIII] is reacted with amine derivative of the formula [XIII] to produce the compound of the formula [XIV].

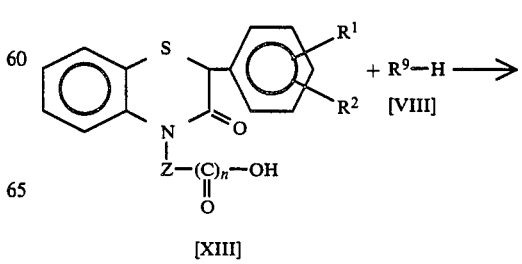

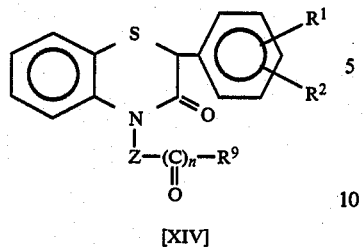

[XIV]

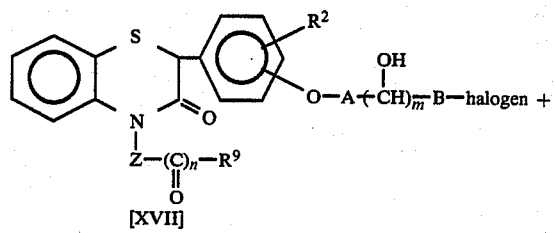

[XVII]

This reaction is performed by Schotten-Baumann method, mixed anhydride method or DCC method which is widely used in peptide synthesis.

When $R^1$ and/or $R^2$ are/is hydroxy, the hydroxy group(s) may be previously protected by ($C_1$-$C_6$) alkanoyl or tetrahydropyranyl and the protective group(s) can be removed by hydrolysis.

(2)-(c) When $R^1$ in the formula [XIV] is hydroxy (represented by the formula [XV]), if necessary, followed by the reaction with halide of the formula [V] which produces the compound of the formula [XVI].

$R^{10}$—H ⟶

[XVIII]

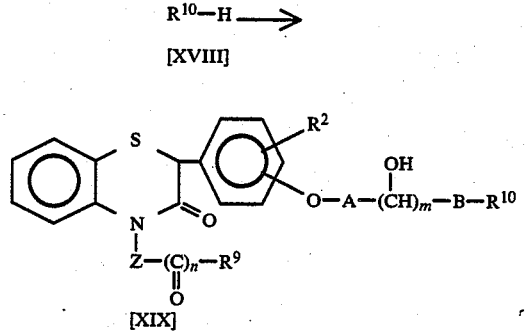

[XIX]

wherein $R^{10}$ is

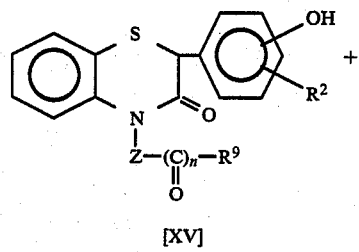

[XV]

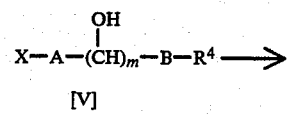

[V]

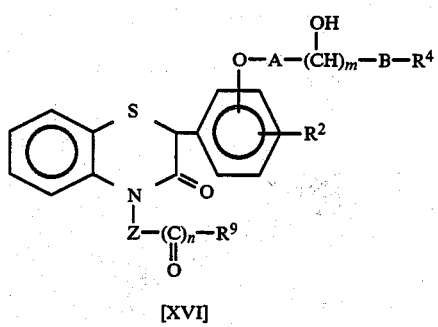

[XVI]

This reaction is performed in the presence of base such as sodium hydride, sodium ethoxide, sodium hydroxide, etc.

(2)-(d) When $R^4$ in the formula [XVI] is halogen (represented by the formula [XVII]), if necessary, further followed by the reaction with amine derivative of the formula [XVIII] which produce the compound of the formula [XIX].

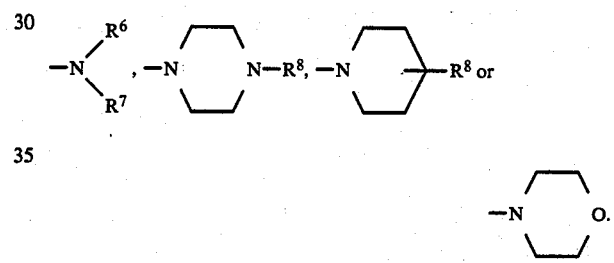

This reaction is performed in the presence of base such as sodium hydride, sodium ethoxide, sodium hydroxide, etc.

(3) Third case: In the formula [I], $R^1$ is hydroxy, $R^3$ is hydrogen, and

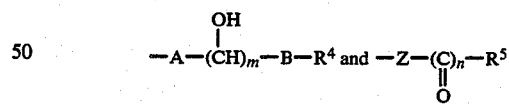

represent the same structure.

The compound of the formula [XX] is reacted with halide of the formula [XXI] to produce the compound of the formula [XXII].

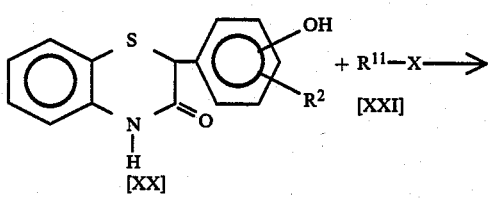

-continued

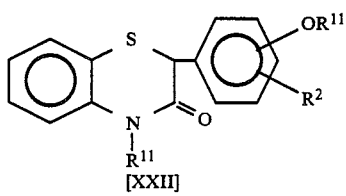

wherein

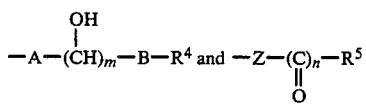

are represented by $R^{11}$.

This reaction is performed, using excess amount of halide of the formula [XXI], in the presence of base such as sodium hydride, sodium ethoxide, sodium hydroxide, etc.

(3)-(a) When $R^{11}$ in the formula [XXII] is $(C_1-C_6)$alkyl containing halogen (represented by the formula [XXIII]), if necessary, followed by the reaction with amine derivative of the formula [VIII] which produces the compound of the formula [XXIV].

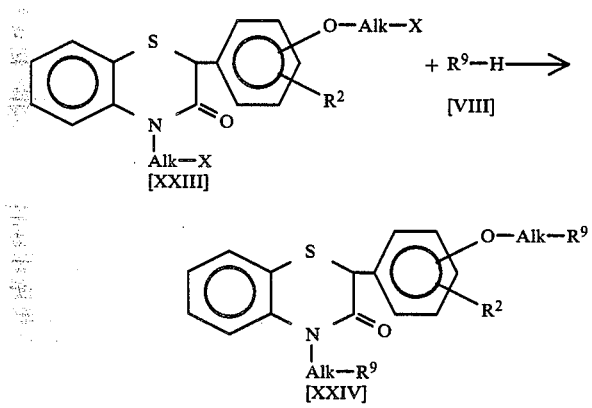

wherein Alk is $(C_1-C_6)$alkylene.

This reaction is performed using excess amount of amine derivative of the formula [VIII] which plays a role of base.

The compounds of this invention can be converted to acid salts. Said salts are obtained by usual methods using inorganic or organic acids. Examples of pharmaceutically acceptable salts of the compounds are hydrochloric acid salt, sulfuric acid salt, phosphoric acid salt, lactic acid salt, maleic acid salt, fumaric acid salt, oxalic acid salt, citric acid salt, methanesulfonic acid salt, benzoic acid salt, p-toluenesulfonic acid salt, etc. The compounds of this invention can be also converted to metal salt or amine salt such as sodium salt, potassium salt, calcium salt, ammonium salt, diethylamine salt, triethanolamine salt, etc.

The compounds of this invention have stereoisomers because of the existence of one or more asymmetric carbon atoms, and these isomers are included in this invention.

Examples are shown below, and the compounds are listed in Table 1-13.

EXAMPLE 1

3,4-Dihydro-2-(4-hydroxyphenyl)-3-oxo-2H-1,4-benzothiazine (compound No. 2)

To a stirred solution of 2-chloro-3,4-dihydro-3-oxo-2H-1,4-benzothiazine (30 g) and phenol (17 g) in anhydrous $CH_2Cl_2$ (400 ml), $AlCl_3$ (24 g) is added by portions under ice-cooling.

The mixture is stirred for 3 hours under ice-cooling and for 2 hours at room temperature, and then poured into ice-water (500 ml). Crystals are collected by filtration to give 30.6 g (79%) of the titled compound.

Physical data are shown in Table 1.

The compounds shown in Table 1 and 2 are prepared by the similar method.

EXAMPLE 2

3,4-Dihydro-2-(2-hydroxy-5-methoxyphenyl)-4-methyl-3-oxo-2H-1,4-benzothiazine (compound No. 3)

To a stirred solution of p-methoxyphenol (37.4 g) in anhydrous $CH_2Cl_2$ (290 ml), 2-chloro-3,4-dihydro-4-methyl-3-oxo-2H-1,4-benzothiazine (53.6 g) is added. The mixture is stirred for 3.5 hours at room temperature. Crystals are collected by filtration to give 56.7 g (75%) of the titled compound.

Physical data are shown in Table 1.

The compounds shown in Table 1 and 2 are prepared by the similar method.

EXAMPLE 3

3,4-Dihydro-4-(3-dimethylaminopropyl)-2-(2-hydroxyphenyl)-3-oxo-2H-1,4-benzothiazine (compound No. 6) and 3,4-dihydro-4-(3-dimethylaminopropyl)-2-(4-hydroxyphenyl)-3-oxo-2H-1,4-benzothiazine (compound No. 71)

To a stirred solution of 2-chloro-3,4-dihydro-4-(3-dimethylaminopropyl)-3-oxo-2H-1,4-benzothiazine (20 g) and phenol (7 g) in anhydrous $CH_2Cl_2$ (200 ml), $AlCl_3$ (10 g) is added under ice-cooling. The mixture is stirred for 3 hours at room temperature and poured into ice-water. The aqueous layer is washed with ether and alkalifized with 6N NaOH. The separated oil is extracted with ethyl acetate and the organic layer is washed with water and saturated sodium chloride solution. The ethyl acetate solution is dried over anhydrous magnesium sulfate and concentrated in vacuo. The residue is chromatographed on silica gel to give 1.7 g (8%) of compound No. 6 and 8.5 g (40%) of compound No. 7.

Physical data are shown in Table 1.

The compound shown in Table 1 is prepared by the similar method.

EXAMPLE 4

[3,4-Dihydro-2-(2-hydroxy-5-nitrophenyl)-3-oxo-2H-1,4-benzothiazin-4-yl]acetic acid (compound No. 16)

To a stirred solution of (2-chloro-3,4-dihydro-3-oxo-1,4-yl-4-benzothiazine)acetic acid (7 g) and p-nitrophenol (4.6 g) in anhydrous $CH_2Cl_2$ (70 ml), $AlCl_3$ (4.4 g) is added. The mixture is stirred under reflux for 8.5 hours, and poured into ice-water and then decantated to give gummy substance. The gummy substance is dissolved in potassium carbonate solution and filtered. The filtrate is washed with $CHCl_3$ and acidified with conc. HCl. The separated oil is extracted with ethyl acetate and the organic layer is washed with saturated sodium chloride solution. The solution is dried over anhydrous sodium sulfate and concentrated in vacuo. Ethanol and benzene are added to the residue to give crystals. The crystals are collected by filtration to give 4 g (41%) of the titled compound.

Physical data are shown in Table 2.

EXAMPLE 5

3,4-Dihydro-3-oxo-2-[4-[(tetrahydropyran-2-yl)oxy]-phenyl]-2H-1,4-benzothiazine (compound No. 5)

To a stirred solution of 3,4-dihydro-2-(4-hydroxyphenyl)-3-oxo-2H-1,4-benzothiazine (compound No. 2, 14 g) and 2,3-dihydropyrane (37.2 ml) in ethyl acetate (120 ml), ethyl acetate (13.6 ml) saturated with HCl gas is added and standed overnight. Saturated sodium hydrogen carbonate solution is added to the mixture and separated crystals are collected by filtration. Ethyl acetate layer of the filtrate is concentrated in vacuo after drying over sodium sulfate. The residue and the crystals are mixed and purified by silica gel column chromatography to give 13.6 g (73%) of the titled compound.

Physical data are shown in Table 1.

EXAMPLE 6

3,4-Dihydro-4-(3-dimethylaminopropyl)-2-(4-hydroxyphenyl)-3-oxo-2H-1,4-benzothiazine (compound No. 7)

To a stirred solution of 50% sodium hydride (0.37 g) in anhydrous dimethylformamide (20 ml), 3,4-dihydro-3-oxo-2-[4-[(tetrahydropyran-2-yl)oxy]phenyl]-2H-1,4-benzothiazine (compound No. 5, 3 g) dissolved in anhydrous dimethylformamide (20 ml) is added under nitrogen atmosphere and ice-cooling, and stirred for 25 minutes. To the mixture, anhydrous dimethylformamide solution of γ-dimethylaminopropyl chloride (prepared from 1.53 g of γ-dimethylaminopropyl chloride hydrochloride and 1.35 ml of triethylamine) is added. The reaction mixture is stirred for 2.5 hours at room temperature and 2 hours at 75° C., poured into a mixture of N HCl and ice-water, and washed with ethyl acetate. The aqueous layer is alkalifized with 30% NaOH and extracted with ethyl acetate. The organic layer is washed with water, dried over anhydrous sodium sulfate and concentrated in vacuo. Ethyl acetate is added to the residue. Separated crystals are collected by filtration to give 2.05 g (68%) of the titled compound.

Physical data are shown in Table 1.

The compounds shown in Table 2 and 3 are prepared by the similar method.

EXAMPLE 7

[3,4-Dihydro-2-(4-methoxyphenyl)-3-oxo-2H-1,4-benzothiazin-4-yl]acetic acid methyl ester (compound No. 32)

To a solution of [3,4-dihydro-2-(4-hydroxyphenyl)-3-oxo-2H-1,4-benzothiazin-4-yl]acetic acid (compound No. 17, 2.5 g) in ethyl acetate (10 ml), diazomethane dissolved in ether is added and standed overnight. The mixture is concentrated in vacuo and the residue is purified by silica gel column chromatography to give 2.5 g (92%) of the titled compound.

Physical data are shown in Table 2.

The compounds shown in Table 2 are prepared by the similar method.

EXAMPLE 8

[3,4-Dihydro-2-(2,5-dimethoxyphenyl)-3-oxo-2H-1,4-benzothiazin-4-yl]acetic acid methyl ester (compound No. 29)

To a solution of [3,4-dihydro-2-(2-hydroxy-5-methoxyphenyl)-3-oxo-2H-1,4-benzothiazin-4-yl]acetic acid (compound No. 14, 2.5 g) in ethyl acetate (20 ml) containing one drop of fluoboric acid, diazomethane dissolved in ether is added and standed overnight. The mixture is concentrated in vacuo to give 1.9 g (70%) of the titled compound.

Physical data are shown in Table 2.

The compounds shown in Table 2 are prepared by the similar method.

EXAMPLE 9

[3,4-Dihydro-2-(2,5-dimethoxyphenyl)-3-oxo-2H-1,4-benzothiazin-4-yl]acetic acid (compound No. 20)

To the solution of [3,4-dihydro-2-(2,5-dimethoxyphenyl)-3-oxo-2H-1,4-benzothiazin-4-yl]acetic acid methyl ester (compound No. 29, 1.4 g) in methanol (20 ml), 2N NaOH (4 ml) is added and stirred for 1 hour. To the mixture, water (50 ml) is added and acidified with N HCl. The reaction product is extracted with ethyl acetate. The orgenic layer is washed with saturated sodium chloride solution, dried over anhydrous sodium sulfate and concentrated in vacuo. Benzene is added to the residue and separated crystals are collected by filtration to give 0.85 g (63%) of the titled compound.

Physical data are shown in Table 2.

The compounds shown in Table 2 are prepared by the similar method.

EXAMPLE 10

[2-(4-Acetoxyphenyl)-3,4-dihydro-3-oxo-2H-1,4-benzothiazin-4-yl]acetic acid (compound No. 26)

To a solution of [3,4-dihydro-2-(4-hydroxyphenyl)-3-oxo-2H-1,4-benzothiazin-4-yl]acetic acid (compound No. 17, 49.2 g) in pyridine (150 ml), acetic anhydride (22 ml) is added and the mixture is standed overnight. The reaction mixture is poured into a mixture of 6N HCl and ice, and the separated oil is extracted with ethyl acetate. The organic layer is washed with N HCl, dried over anhydrous sodium sulfate and concentrated in vacuo. Benzene and ether are added to the residue and separated crystals are collected by filtration to give 34.9 g (63%) of the titled compound.

Physical data are shown in Table 2.

The compound shown in Table 2 is prepared by the similar method.

EXAMPLE 11

[2-(4-Acetoxyphenyl)-3,4-dihydro-3-oxo-2H-1,4-benzothiazin-4-yl]acetamide (compound No. 37)

To a stirred solution of [2-(4-acetoxyphenyl)-3,4-dihydro-3-oxo-2H-1,4-benzothiazin-4-yl]acetic acid (compound No. 26, 4.6 g) and triethylamine (1.8 ml) in $CH_2Cl_2$ (45 ml), isobutylchloroformate (1.7 ml) is added dropwise at −12° C. After the addition, the reaction mixture is stirred for 10 minutes at the same temperature. Conc. ammonia water (7.2 ml) is added to the mixture. The mixture is stirred for 30 minutes at room temperature, and washed with saturated sodium hydrogen carbonate solution and N HCl. The organic layer is dried over anhydrous sodium sulfate and concentrated in vacuo to give 3.5 g (76%) of the titled compound.

Physical data are shown in Table 3.

The compounds shown in Table 3 are prepared by the similar method.

EXAMPLE 12

[3,4-Dihydro-2-(4-hydroxyphenyl)-3-oxo-2H-1,4-benzothiazin-4-yl]acetamide (compound No. 35)

To a stirred solution of [2-(4-acetoxyphenyl)-3,4-dihydro-3-oxo-2H-1,4-benzothiazin-4-yl]acetamide (compound No. 37, 3.5 g) in dioxane (20 ml) and ethanol (30 ml), 2N NaOH (25 ml) is added under ice-water cooling. The mixture is stirred for 5 minutes and acidified with 6N HCl. The separated oil is extracted with ethyl acetate and the organic layer is washed with saturated sodium hydrogen carbonate. The organic layer is dried over anhydrous sodium sulfate and concentrated in vacuo.

Benzene is added to the residue and separated crystals are collected by filtration to give 2.4 g (78%) of the titled compound.

Physical data are shown in Table 3.

The compound shown in Table 3 are prepared by the similar method.

EXAMPLE 13

3,4-Dihydro-2-(4-hydroxyphenyl)-4-morpholinocarbonylmethyl-3-oxo-2H-1,4-benzothiazine (compound No. 45)

To a stirred solution of [2-(4-acetoxyphenyl)-3,4-dihydro-3-oxo-2H-1,4-benzothiazin-4-yl]acetic acid (compound No. 26, 4 g) and triethylamine (1.6 ml) in anhydrous CH$_2$Cl$_2$ (40 ml), isobutylchloroformate (1.5 ml) is added dropwise at −12° C. After the addition, the reaction mixture is stirred for 15 minutes at the same temperature. Morpholine (4.9 ml) is added to the mixture and the mixture is stirred for 1.5 hours at room temperature and poured into 2N NaOH. The aqueous layer is acidified with N HCl and separated crystals are collected by filtration. The crystals are washed with sodium hydrogen carbonate solution, water and ethanol to give 2.08 g (48%) of the titled compound.

Physical data are shown in Table 3.

The compounds shown in Table 3 are prepared by the similar method.

EXAMPLE 14

3,4-Dihydro-4-[4-(2-hydroxyethyl)piperazinocarbonylmethyl]-2-(4-hydroxyphenyl)-3-oxo-2H-1,4-benzothiazine (compound No. 44)

To a stirred solution of [2-(4-acetoxyphenyl)-3,4-dihydro-3-oxo-2H-1,4-benzothiazin-4-yl]acetic acid (compound No. 26, 2.9 g) and triethylamine (1.2 ml) in anhydrous CH$_2$Cl$_2$ (30 ml), isobutylchloroformate (1.1 ml) is added dropwise at −18° C. After the addition, the reaction mixture is stirred for 20 minutes at the same temperature. 1-[2-[(Tetrahydropyran-2-yl)oxy]ethyl]piperazine (2.6 g) is added to the mixture, and the mixture is stirred for 2.5 hours at room temperature, poured into N HCl and washed with ethyl acetate. The aqueous layer is alkalifized with 2N NaOH and stirred for 1 hour. The separated oil is extracted with ethyl acetate, and the organic layer is washed with water, dried over anhydrous sodium sulfate and concentrated in vacuo. CHCl$_3$ is added to the residue and separated crystals are collected by filtration to give 2.4 g (69%) of the titled compound.

Physical data are shown in Table 3.

EXAMPLE 15

3,4-Dihydro-2-[2-(2,3-epoxypropoxy)-5-methoxyphenyl]-3-oxo-2H-1,4-benzothiazine (compound No. 10)

To a stirred solution of 3,4-dihydro-2-(2-hydroxy-5-methoxyphenyl)-3-oxo-2H-1,4-benzothiazine (compound No. 1, 5.2 g) in methanol (30 ml), N NaOH (26 ml) and epichlorohydrine (7 ml) are added. The reaction mixture is stirred for 30 minutes at 50° C. and overnight at room temperature.

Ethyl acetate is added to the mixture, and the organic layer is washed with saturated sodium chloride solution, dried over anhydrous sodium sulfate and concentrated in vacuo. The residual oil is purified by silica gel column chromatography to give 2.9 g (47%) of the titled compound.

Physical data are shown in Table 1.

The compounds shown in Table 1 and 3 are prepared by the similar method.

EXAMPLE 16

[3,4-Dihydro-2-[2-(2,3-epoxypropoxy)-5-methoxyphenyl]-3-oxo-2H-1,4-benzothiazin-4-yl]acetamide (compound No. 39)

To a solution of 50% sodium hydride (0.19 g) in anhydrous dimethylformamide (5 ml), [3,4-dihydro-2-(2-hydroxy-5-methoxyphenyl)-3-oxo-2H-1,4-benzothiazin-4-yl]acetamide (compound No. 34, 1.5 g) in anhydrous dimethylformamide (15 ml) is added under nitrogen atmosphere. After the addition, epichlorohydrine (1.4 ml) is added to the reaction mixture, and the mixture is stirred for 1 hour at room temperature and for 30 minutes at 50° C. The mixture is poured into ice-water and the separated oil is extracted with ethyl acetate. The organic layer is washed with water, N NaOH and water, dried over anhydrous sodium sulfate and concentrated in vacuo. Methanol and isopropylether are added to the residue and separated crystals are collected by filtration to give 1.39 g (80%) of the titled compound.

Physical data are shown in Table 3.

The compounds shown in Table 1 and 3 are prepared by the similar method.

EXAMPLE 17

2-[2-(3-Chloropropoxy)-5-methoxyphenyl]-3,4-dihydro-2H-1,4-benzothiazine (compound No. 46)

To a stirred solution of 50% sodium hydride (6.2 g) in anhydrous dimethylformamide (20 ml), 3,4-dihydro-2-(2-hydroxy-5-methoxyphenyl)-3-oxo-2H-1,4-benzothiazine (compound No. 1, 28.7 g) dissolved in anhydrous dimethylformamide (100 ml) is added dropwise. After the addition, 3-chloropropylbromide (31.5 g) dissolved in anhydrous ethanol (50 ml) is added and the reaction mixture is stirred continuously for 6 hours. The mixture is poured into water (800 ml) and separated oil is extracted with ethyl acetate (300 ml). The organic layer is washed with water and saturated sodium chloride solution, dried over anhydrous sodium sulfate and concentrated in vacuo. The residual oil is purified by silica gel column chromatography to give 15.6 g (43%) of the titled compound.

Physical data are shown in Table 4.

The compounds shown in Table 4,5 and 9 are prepared by the similar method.

EXAMPLE 18

3,4-Dihydro-2-[4-(3-dimethylaminopropoxy)phenyl]-4-methyl-3-oxo-2H-1,4-benzothiazine (compound No. 72)

To a stirred solution of 50% sodium hydride (1.2 g) in anhydrous dimethylformamide (5 ml), 3,4-dihydro-2-(4-hydroxyphenyl)-4-methyl-3-oxo-2H-1,4-benzothiazine (compound No. 4, 3.0 g) and 3-dimethylaminopropyl chloride (2.1 g) dissolved in anhydrous dimethylformamide (12 ml) are added dropwise under nitrogen atmosphere.

After the addition, the reaction mixture is stirred for 1 hour at room temperature and for 3.5 hours at 85°–90° C., and poured into water (100 ml). Reaction product is extracted with benzene, and the organic layer is washed with N KOH and saturated sodium chloride solution, dried over anhydrous sodium sulfate and concentrated in vacuo. The residual oil is purified by silica gel column chromatographyl to give 1.5 g (38%) of the titled compound.

Physical data are shown in Table 7.

The compounds shown in Table 6, 7, and 9–12 are prepared by the similar method.

EXAMPLE 19

3,4-Dihydro-2-[5-methoxy-2-[4-(N-methylcyclohexylamino)butoxy]phenyl]-4-methyl-3-oxo-2H-1,4-benzothiazine oxalate (compound No. 63)

3,4-Dihydro-2-[2-(4-bromobutoxy)-5-methoxyphenyl]-4-methyl-3-oxo-2H-1,4-benzothiazine (compound No. 50, 1.1 g) and N-methylcyclohexylamine (3.4 g) are dissolved in benzene (1 ml), and the mixture is stirred for 2 hours at 105°–110° C. After cooling, N HCl (30 ml) is added to the mixture and the reaction product is extracted with chloroform. The organic layer is washed with N HCl, water and N NaOH, dried over anhydrous sodium sulfate and concentrated in vacuo. The residual oil is dissolved in ethyl acetate (30 ml). Oxalic acid (0.3 g) dissolved in ethyl acetate (10 ml) is added to the solution with stirring. Separated crystals are collected by filtration to give 1.1 g (78%) of the titled compound.

Physical data are shown in Table 6.

The compounds shown in Table 6–11 are prepared by the similar method.

EXAMPLE 20

3,4-Dihydro-2-[5-methoxy-2-[3-[4-(3,4,5-trimethoxyphenethyl)piperazino]propoxy]phenyl]-3-oxo-2H-1,4-benzothiazine hydrochloride (compound No. 74)

Acetone (10 ml) solution of 2-[2-(3-chloropropoxy)-5-methoxyphenyl]-3,4-dihydro-3-oxo-2H-1,4-benzothiazine (1.0 g) and sodium iodide (0.4 g) is refluxed for 30 minutes. Precipitate is filtered off and the filtrate is concentrated in vacuo. To the residue, 1-(3,4,5-trimethoxyphenetyl)piperazine (1.0 g), sodium carbonate (0.5 g) and toluene (5 ml) are added and the mixture is refluxed for 4 hours. After cooling, chloroform (30 ml) is added to the reaction mixture. The organic layer is washed with N HCl, N NaOH and saturated sodium chloride solution, dried over sodium sulfate and concentrated in vacuo. The residual oil is dissolved in ethyl acetate, and to the solution HCl/ethyl acetate is added. Separated crystals are collected by filtration to give 1.2 g (64%) of the titled compound.

Physical data are shown in Table 8.

The compounds shown in Table 6–12 are prepared by the similar method.

EXAMPLE 21

2-[4-(3-Chloropropoxy)phenyl]-3,4-dihydro-4-(3-dimethylaminopropyl)-3-oxo-2H-1,4-benzothiazine (compound No. 88)

To a stirred solution of 50% sodium hydride (0.33 g) in anhydrous dimethylformamide (10 ml), 3,4-dihydro-4-(3-dimethylaminopropyl)-2-(4-hydroxyphenyl)-3-oxo-2H-1,4-benzothiazine (comopund No. 7, 2.15 g) dissolved in anhydrous dimethylformamide (10 ml) is added dropwise and the reaction mixture is stirred for 15 minutes. To the mixture, 1-bromo-3-chloropropane (2.27 g) dissolved in anhydrous ethanol (7 ml) is added and the mixture is stirred for 2 hours at room temperature and for 3 hours at 40° C. The mixture is poured into ice-water and the reaction product is extracted with ethyl acetate. The organic layer is washed with N NaOH, water and saturated sodium chloride solution, dried over anhydrous magnesium sulfate and concentrated in vacuo. The residue is purified by silica gel column chromatography to give 1.31 g (50%) of the titled compound.

The physical data are shown in Table 10.

The compounds shown in Table 4, 5 and 10–11 are prepared by the similar method.

EXAMPLE 22

4-(6-Chlorohexyl)-2-[4-(6-chlorohexyloxy)phenyl]-3,4-dihydro-3-oxo-2H-1,4-benzothiazine (compound No. 87)

To a stirred solution of 50% sodium hydride (1.0 g) in anhydrous dimethylformamide (5 ml), 3,4-dihydro-2-(4-hydroxyphenyl)-3-oxo-2H-1,4-benzothiazine (compound No. 2, 2.6 g) dissolved in anhydrous dimethylformamide (12 ml) is added dropwise under nitrogen atmosphere and the reaction mixture is stirred for 5 minutes. To the mixture, 6-chlorohexyl methanesulfonate (5.1 g) is added, and the mixture is stirred for 3 hours at room temperature and poured into ice-water. The reaction product is extracted with ethyl acetate.

The organic layer is washed with N KOH, water and saturated sodium chloride solution, dried over magnesium sulfate and concentrated in vacuo. The residue is purified by silica gel column chromatography to give 3.5 g (70%) of the titled compound.

Physical data are shown in Table 10.

The compounds shown in Table 9 and 10 are prepared by the similar method.

EXAMPLE 23

3,4-Dihydro-2-[2-(3-dimethylaminopropoxy)-5-methoxyphenyl]-4-(3-dimethylaminopropyl)-3-oxo-2H-1,4-benzothiazine dioxalate (compound No. 82)

To a stirred solution of 50% sodium hydride (3 g) in anhydrous dimethylformamide, anhydrous ethanol (10 ml) is added dropwise. To the mixture, 3,4-dihydro-2-(2-hydroxy-5-methoxyphenyl)-3-oxo-2H-1,4-benzothiazine (compound No. 1, 4 g) dissolved in anhydrous dimethylformamide (15 ml) and then γ-dimethylaminopropyl chloride hydrochloride (5 g) dissolved in anhydrous dimethylformamide (12 ml) is added, and the reaction mixture is stirred for 5.5 hours at 60° C. The mixture is poured into water and the reaction product is extracted with ethyl acetate. The organic layer is washed with N KOH, water and saturated sodium chloride solution, dried over anhydrous sodium sulfate and concentrated in vacuo. The residue is purified by silica gel column chromatography to give 4.2 g (66%) of the titled compound as free form.

The product is dissolved in ethyl acetate, and to the solution oxalic acid is added to give 5.1 g (57%) of the titled compound.

Physical data are shown in Table 9.

The compounds shown in Table 9 and 10 are prepared by the similar method.

EXAMPLE 24

3,4-Dihydro-4-(5-dimethylaminopentyl)-2-[2-(5-dimethylaminopentyloxy)-5-methoxyphenyl]-3-oxo-2H-1,4-benzothiazine dicitrate (compound No. 84)

A mixture of 4-(5-bromopentyl)-2-[2-(5-bromopentyloxy)-5-methoxyphenyl]-3,4-dihydro-3-oxo-2H-1,4-benzothiazine (compound No. 80, 0.55 g), 40% dimethylamine aqueous solution (1.3 ml) and benzene (1 ml) is refluxed for 4.5 hours with stirring. Chloroform is added to the reaction mixture, and the organic layer is washed with water, N NaOH and saturated sodium chloride solution, dried over anhydrous magnesium sulfate and concentrated in vacuo. The residue is purified by silica gel column chromatography to give 0.3 g (62%) of the titled compound as free form. The product is dissolved in ethyl acetate, and to the solution citric acid is added to give 0.35 g (41%) of the titled compound.

Physical data are shown in Table 9.

The compounds shown in Table 9 and 10 are prepared by the similar method.

EXAMPLE 25

[3,4-Dihydro-2-[2-(3-dimethylaminopropoxy)-5-methoxyphenyl]-3-oxo-2H-1,4-benzothiazin-4-yl]acetamide (compound No. 93)

To a stirred solution of [2-[2-(3-chloropropoxy)-5-methoxyphenyl]-3-oxo-2H-1,4-benzothiazin-4-yl]acetamide (compound No. 92, 1.5 g) and potassium iodide (0.3 g) in dimethylformamide (5 ml), 40% aqueous dimethylamine (2.4 ml) is added. The reaction mixture is stirred for 2.5 hours at 60° C. and poured into water. The reaction product is extracted with ethyl acetate. The organic layer is washed with water, dried over anhydrous sodium sulfate and concentrated in vacuo. Benzene is added to the residue and separated crystals are collected by filtration to give 1.22 g (80%) of the titled compound.

Physical data are shown in Table 11.

The compounds shown in Table 11 and 12 are prepared by the similar method.

EXAMPLE 26

3,4-Dihydro-4-[[4-(ethoxycarbonyl)piperazino]carbonylmethyl]-2-[4-[3-[4-(4-fluorobenzoyl)piperizino]-propoxy]phenyl]-3-oxo-2H-1,4-benzothiazine (compound No. 104)

A solution of 2-[4-(3-chloropropoxy)phenyl]-3,4-dihydro-4-[[4-(ethoxycarbonyl)piperazino]carbonylmethyl]-3-oxo-2H-1,4-benzothiazine (compound No. 103, 0.9 g) and sodium iodide (0.25 g) in acetone (5 ml) is refluxed for 1 hour. Precipitate is filtered off and the filtrate is concentrated in vacuo.

To the residue, 4-(4-fluorobenzoyl)piperidine (0.7 g), potassium carbonate (0.51 g) and dimethylformamide (5 ml) are added and the mixture is stirred for 1 hour at 50° C. The mixture is poured into water and the reaction product is extracted with chloroform. The organic layer is washed with water, dried over anhydrous sodium sulfate and concentrated in vacuo. The residue is purified by silica gel column chromatography to give 0.79 g (66%) of the titled compound.

Physical data are shown in Table 12.

EXAMPLE 27

2-[2-(3-tert-Butylamino-2-hydroxypropoxy)-5-methoxyphenyl]-3,4-dihydro-3-oxo-2H-1,4-benzothiazine (compound No. 105)

3,4-Dihydro-2-[2-(2,3-epoxypropoxy)-5-methoxyphenyl]-3-oxo-2H-1,4-benzothiazine (compound No. 10, 0.8 g) and tert-butylamine (2.5 ml) are dissolved in ethanol (15 ml). The solution is refluxed for 1.5 hours, and after cooling, concentrated in vacuo. The residue is dissolved in chloroform, and the solution is washed with 2N HCl, water and N NaOH. The organic layer is dried over anhydrous sodium sulfate and concentrated in vacuo to give 0.9 g (93%) of the titled compound.

Physical data are shown in Table 13.

The compounds shown in Table 13 are prepared by the similar method.

EXAMPLE 28

3,4-Dihydro-2-[5-methoxy-2-[2-hydroxy-3-(4-phenacylpiperazino)propoxy]phenyl]-4-methyl-3-oxo-2H-1,4-benzothiazine dimaleate (compound No. 107)

3,4-Dihydro-2-[2-(2,3-epoxypropoxy)-5-methoxyphenyl]-4-methyl-3-oxo-2H-1,4-benzothiazine (compound No. 11, 1.6 g) and phenacylpiperazine (1.0 g) are dissolved in toluene (1 ml). The solution is stirred for 1.5 hours at 110°–120° C. After cooling, 2N HCl (10 ml) is added to the reaction mixture and stirred. Supernatant liquid is removed off by decantation. To the residual gummy product, chloroform (30 ml) and N NaOH (15 ml) are added. The organic layer is dried over anhydrous sodium sulfate and concentrated in vacuo. To the residual oil dissolved in ethyl acetate, maleic acid (1.1 g) is added. Separated crystals are collected by filtration to give 3.0 g (84%) of the titled compound.

Physical data are shown in Table 13.

EXAMPLE 29

3,4-Dihydro-2-[2-(3-dimethylaminopropoxy)-5-methoxyphenyl]-4-(3-dimethylaminopropyl)-3-oxo-2H-1,4-benzothiazine dioxalate (compound No. 82)

To a stirred solution of 50% sodium hydride (0.24 g) in anhydrous dimethylformamide (5 ml), 3,4-dihydro-2-[2-(3-dimethylaminopropoxy)-5-methoxyphenyl]-3-oxo-2H-1,4-benzothiazine (compound No. 55, 0.74 g) dissolved in anhydrous dimethylformamide (5 ml) is added dropwise under nitrogen atmosphere, and the mixture is stirred continuously for 10 minutes.

To the reaction mixture, γ-dimethylaminopropyl chloride hydrochloride (0.47 g) dissolved in anhydrous dimethylformamide (3 ml) is added and the mixture is stirred overnight at room temperature. The mixture is poured into water and the reaction product is extracted with ethyl acetate. The organic layer is washed with N KOH, water and saturated sodium chloride solution, dried over anhydrous sodium sulfate and concentrated in vacuo. The residue is purified by silica gel column chromatography. The product is dissolved in ethyl acetate, and to the solution oxalic acid is added to give 1.1 g (87%) of the titled compound.

Physical data are shown in Table 9.

Following compounds can be prepared by similar methods described in Example 1–29.

3,4-Dihydro-4-(3-dimethylaminopropyl)-2-[2-[3-(N-methylcyclohexylamino)propoxy]-5-methoxyphenyl]-3-oxo-2H-1,4-benzothiazine 3,4-Dihydro-4-(3-dimethylaminopropyl)-2-[2-[4-(N-methylcyclohexylamino)butoxy]-5-methoxyphenyl]-3-oxo-2H-1,4-benzothiazine 3,4-Dihydro-2-[2-(4-dimethylaminobutoxy)-5-methoxyphenyl]-4-(3-dimethylaminopropyl)-3-oxo-2H-1,4-benzothiazine 3,4-Dihydro-4-(3-dimethylaminopropyl)-2-[4-[3-(N-methylcyclohexylamino)propoxy]phenyl]-3-oxo-2H-1,4-benzothiazine 3,4-Dihydro-4-(3-dimethylaminopropyl)-2-[4-[4-(N-methylcyclohexylamino)butoxy]phenyl]-3-oxo-2H-1,4-benzothiazine 3,4-Dihydro-2-[4-(4-dimethylaminobutoxy)phenyl]-4-(3-dimethylaminopropyl)-3-oxo-2H-1,4-benzothaizine 2-[2-[4-(4-Benzoylpiperidino)butoxy]-5-methoxyphenyl]-3,4-dihydro-4-(3-dimethylaminopropyl)-3-oxo-2H-1,4-benzothiazine 3,4-Dihydro-4-(3-dimethylaminopropyl)-2-[5-methoxy-2-[4-[4-(3,4,5-trimethoxyphenethyl)piperazino]butoxy]phenyl]-3-oxo-2H-1,4-benzothiazine 3,4-Dihydro-4-(3-dimethylaminopropyl)-2-[2-[4-[4-(4-fluorobenzoyl)piperidino]butoxy]-5-methoxyphenyl]-3-oxo-2H-1,4-benzothiazine 2-[4-(3-tert-Butylamino-2-hydroxypropoxy)phenyl]-3,4-dihydro-3-oxo-2H-1,4-benzothiazine 3,4-Dihydro-2-[4-[3-(N-methylcyclohexylamino)propoxy]phenyl]-4-[3-(N-methylcyclohexylamino)propyl]-3-oxo-2H-1,4-benzothiazine 3,4-Dihydro-2-[4-[3-(N-methylcyclohexylamino)propoxy]phenyl]-3-oxo-2H-1,4-benzothiazine 3,4-Dihydro-2-[4-(3-dimethylaminopropoxy)phenyl]-4-[2-[4-(2-hydroxyethyl)piperazino]-2-oxoethyl]-3-oxo-2H-1,4-benzothiazine

[3,4-Dihydro-2-[2-[4-(N-methylcyclohexylamino)butoxy]-5-methoxyphenyl]-3-oxo-2H-1,4-benzothaizine-4-yl]-N,N-dimethylacetamide 3,4-Dihydro-2-[4-[3-[4-[2-hydroxy-2-(4-methoxyphenyl)ethyl]piperazino]propoxy]phenyl]-3-oxo-2H-1,4-benzothiazine 3,4-Dihydro-2-[4-[4-[4-(4-fluorobenzoyl)piperidino]butoxy]phenyl]-3-oxo-2H-1,4-benzothiazine 2-[4-[4-(4-Benzoylpiperidino)butoxy]phenyl]-3,4-dihydro-3-oxo-2H-1,4-benzothiazine 3,4-Dihydro-2-[2-[4-[4-(2-hydroxy-2-phenylethyl)piperazino]butoxy]-5-methoxyphenyl]-3-oxo-2H-1,4-benzothiazine 3,4-Dihydro-4-(3-dimethylaminopropyl)-2-[2-[4-[4-(2-hydroxy-2-phenylethyl)piperazino]butoxy]-5-methoxyphenyl]-3-oxo-2H-1,4-benzothiazine

TABLE 1

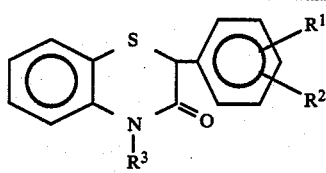

| Compound No. | R³ | R¹ | R² | Method (Example No.) | Yield (%) | mp (°C.) | IR (KBr, cm⁻¹) |
|---|---|---|---|---|---|---|---|
| 1 | H | 2-OH | 5-OCH₃ | 1 | 84 | 216–219 (dec.) (DMF—H₂O) | 3336, 1637, 1580, 1506, 1473, 1427, 1345, 1267, 1210, 1187, 1047, 809, 756, 645 |
| | | | | 2 | 68 | | |
| 2 | H | 4-OH | H | 1 | 79 | 197–201 (EtOH) | 3280, 1636, 1608, 1579, 1507, 1478, 1390, 1265, 1244, 1219, 831, 753 |
| | | | | 2 | 57 | | |
| 3 | —CH₃ | 2-OH | 5-OCH₃ | 1 | 88 | 202–205 (DMF—H₂O) | 3280, 1629, 1582, 1508, 1445, 1425, 1374, 1302, 1266, 1202, 1150, 1039, 809, 749 |
| | | | | 2 | 75 | | |
| 4 | —CH₃ | 4-OH | H | 1 | 63 | 158–162 (EtOH) | 3272, 1637, 1610, 1583, 1441, 1360, 1217, 746, 690, 656 |
| | | | | 2 | 51 | | |
| | | | | 6 | 74 | | |
| 5 | H | 4-O-(tetrahydropyran-2-yl) | H | 5 | 73 | 161–163 | 3200, 2928, 1665, 1581, 1509, 1477, 1362, 1357, 1234, 1174, 1032, 962m 746 |
| 6 | —(CH₂)₃N(CH₃)₂ | 2-OH | H | 2 | 3 | 161–165 (dec.) (EtOH) | 2940, 1654, 1581, 1445, 1376, 1316, 1271, 1250, 1223, 757 |
| | | | | 3 | 8 | | |
| 7 | —(CH₂)₃N(CH₃)₂ | 4-OH | H | 2 | 25 | 158–160 | 2932, 1654, 1607, 1586, 1473, 1466, 1443, 1368, 1257, 1240, 1206, 1168, |
| | | | | 3 | 40 | | |
| | | | | 6 | 68 | | |
| 8 | —(CH₂)₃N(CH₃)₂ | 2-OH | 5-OCH₃ | 2 | 83 | oil | 2944, 1735, 1656, 1509, 1474, 1460, 1444, 1371, 1270, 1225, 1218, 1040, 750 (neat) |
| | | | | 3 | 91 | | |
| 9 | —(CH₂)₃N(CH₃)₂ | 4-O—CH₂—CH(—O—)CH₂ (epoxide) | H | 15 | 36 | amorph. | 1661, 1608, 1584, 1509, 750 |
| | | | | 16 | 56 | | |
| 10 | H | 2-O—CH₂—CH(—O—)CH₂ (epoxide) | 5-OCH₃ | 15 | 47 | 141–144 | 3184, 3044, 1663, 1237, 1209, 798 |
| | | | | 16 | 69 | | |

TABLE 1-continued

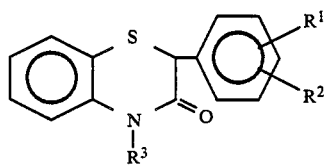

| Compound No. | R³ | R¹ | R² | Method (Example No.) | Yield (%) | mp (°C.) | IR (KBr, cm⁻¹) |
|---|---|---|---|---|---|---|---|
| 11 | —CH₃ | 2-O—CH₂CH——CH₂ (O epoxide) | 5-OCH₃ | 15 | 84 | 139–143 | 3050, 1643, 1242, 1217, 814 |
|  |  |  |  | 16 | 91 |  |  |

TABLE 2

| Compound No. | R | R¹ | R² | Method (Example No.) | Yield (%) | mp (°C.) | IR (KBr, cm⁻¹) |
|---|---|---|---|---|---|---|---|
| 12 | H | 2-OH | 5-CH₃ | 1 | 80 | 182–183 (dec.) (MeOH—AcOEt—C₆H₆) | 3056, 1733, 1620, 1578, 1509, 1479, 1448, 1390, 1256, 1198, 810, 750 |
|  |  |  |  | 2 | 75 |  |  |
| 13 | H | 2-OH | 5-OH | 1 | 57 | 211–211.5 (dec.) (MeOH—H₂O) | 3276, 1725, 1653, 1364, 1319, 1267, 1207, 824, 750 |
|  |  |  |  | 2 | 52 |  |  |
| 14 | H | 2-OH | 5-OCH₃ | 1 | 71 | 190–191 (dec.) (EtOH—C₆H₆) | 3084, 1751, 1734, 1625, 1578, 1508, 1448, 1430, 1388, 1259, 1193, 1042, 751 |
|  |  |  |  | 2 | 58 |  |  |
| 15 | H | 2-OH | 5-Cl | 1 | 67 | 217 (dec.) (MeOH—AcOEt—C₆H₆) | 3400, 1708, 1642, 1583, 1500, 1482, 1445, 1408, 1368, 1282, 1236, 1209, 1107, 810, 749 |
|  |  |  |  | 2 | 58 |  |  |
| 16 | H | 2-OH | 5-NO₂ | 1 | 18 | 253 (dec.) (MeOH—AcOEt—C₆H₆) | 3300, 1707, 1629, 1588, 1524, 1500, 1482, 1432, 1411, 1375, 1335, 1285, 1248, 1213, 1080, 746, 635 |
|  |  |  |  | 2 | 3 |  |  |
|  |  |  |  | 4 | 41 |  |  |
| 17 | H | 4-OH | H | 1 | 83 | 188–191 (dec.) | 3396, 3176, 3020, 1705, 1654, 1608, 1369, 1265, 1240, 1206, 749 |
|  |  |  |  | 2 | 75 |  |  |
|  |  |  |  | 6 | 64 |  |  |
| 18*¹ | H | 4-OH | 3-OH | 1 | 60 | 136–138 (dec.) (MeOH—AcOEt) | 3324, 1720, 1647, 1610, 1527, 1479, 1444, 1373, 1293, 1232, 1197, 746 |
|  |  |  |  | 2 | 53 |  |  |
| 19*² | H | 2-OCH₃ | 5-CH₃ | 9 | 99 | 113–114 (dec.) (Et₂O—C₆H₆) | 3048, 1722, 1661, 1501, 1479, 1445, 1401, 1368, 1320, 1241, 1214, 1202, 1027, 806, 757, 691 |
| 20 | H | 2-OCH₃ | 5-OCH₃ | 9 | 63 | 144–146 (CH₂Cl₂—Et₂O—C₆H₆) | 3420, 1726, 1708, 1663, 1500, 1482, 1447, 1368, 1317, 1243, 1222, 1042, 753 |
| 21*² | H | 2-OCH₃ | 5-Cl | 9 | 94 | 119–121 (dec.) (C₆H₆) | 3056, 1720, 1661, 1479, 1368, 1237, 1217, 1193, 1023, 808, 762, 693 |
| 22*³ | H | 2-OCH₃ | 5-NO₂ | 9 | 99 | 186–188 (dec.) (CH₃COCH₃—CHCl₃—C₆H₆) | 3620, 3412, 1720, 1664, 1587, 1505, 1485, 1371, 1339, 1266, 1237, 1190, 1018, 757, 750 |
| 23*⁴ | H | 4-OCH₃ | H | 9 | 67 | 58–61 (Et₂O—C₆H₆) | 3420, 1724, 1664, 1608, 1581, 1510, 1478, 1447, 1367, 1314, 1302, 1242, 1207, 1175, 1024, 750, 677 |
| 24*⁵ | H | 4-OCH₃ | 3-OCH₃ | 9 | 80 | 208–210 | 3484, 1631, 1599, 1511, 1478, 1439, 1420, 1397, 1370, 1301, 1281, 1260, 1232, 1140, 1021, 749 |
| 25 | H | 2-OCOCH₃ | 5-OCH₃ | 10 | 86 | amorph. | 1750, 1741, 1735, 1663, 1478, 1369, 1189 |
| 26 | H | 4-OCOCH₃ | H | 10 | 63 | 170–172 | 3032, 3016, 2924, 1734, 1718, 1658, 1479, 1442, 1400, 1366, 1196, 1167, 749 |
| 27 | H | 4-N(CH₃)₂ | H | 1 | 34 | amorph. | 3408, 1719, 1660, 1609, 1583, 1519, 1478, 1445, 1369, 1320, 1201, 1161, 748 |
|  |  |  |  | 2 | 45 |  |  |
| 28 | —CH₃ | 2-OCH₃ | 5-CH₃ | 7 | 33 | 97–98 | 1744, 1663, 1502, 1365, 1245, 1214, 1180, 1027, 803, 750 |
|  |  |  |  | 8 | 70 | (MeOH) |  |
| 29 | —CH₃ | 2-OCH₃ | 5-OCH₃ | 7 | 26 | 127.5–128.5 (CH₂Cl₂—MeOH) | 1744, 1738, 1655, 1498, 1239, 1219, 1180, 1035, 749 |
|  |  |  |  | 8 | 70 |  |  |
| 30 | —CH₃ | 2-OCH₃ | 5-Cl | 7 | 40 | 139–140 (AcOMe—MeOH) | 1744, 1664, 1366, 1241, 1220, 1022, 752 |
|  |  |  |  | 8 | 87 |  |  |
| 31 | —CH₃ | 2-OCH₃ | 5-NO₂ | 7 | 52 | 187–188 (AcOMe—MeOH) | 1745, 1736, 1664, 1586, 1510, 1369, 1338, 1264, 1220, 1194, 1089, 1017, |
|  |  |  |  | 8 | 99 |  |  |

TABLE 2-continued

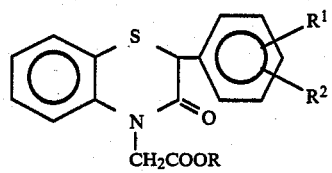

| Compound No. | R | R¹ | R² | Method (Example No.) | Yield (%) | mp (°C.) | IR (KBr, cm⁻¹) |
|---|---|---|---|---|---|---|---|
| 32 | —CH₃ | 4-OCH₃ | H | 7<br>8 | 92<br>98 | oil | 825, 760, 750<br>1747, 1668, 1609, 1584, 1513, 1481, 1448, 1368, 1249, 1210, 1178, 1028, 750 (neat) |
| 33 | —CH₃ | 4-OCH₃ | 3-OCH₃ | 7<br>8 | 31<br>81 | oil | 1750, 1669, 1586, 1516, 1369, 1263, 1212, 1183, 1140, 1025, 750 (neat) |

*¹Contains ½ molecules of ethyl acetate.
*²Contains ½ molecules of benzene.
*³Contains ½ molecules of benzene.
*⁴Contains one molecule of benzene.
*⁵½ calcium salt.monohydrate.

TABLE 3

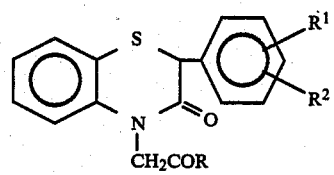

| Compound No. | R | R¹ | R² | Method (Example No.) | Yield (%) | mp (°C.) | IR (KBr, cm⁻¹) |
|---|---|---|---|---|---|---|---|
| 34 | —NH₂ | 2-OH | 5-OCH₃ | 12<br>13 | 97<br>63 | 237–241 (dec.)<br>(CH₃COCH₃—H₂O) | 3440, 3308, 3288, 3188, 2924, 1682, 1653, 1606, 1584, 1508, 1478, 1443, 1428, 1371, 1303, 1280, 1272, 1258, 1219, 1201, 1033, 750, 730, 554 |
| 35 | —NH₂ | 4-OH | H | 6<br>12<br>13 | 59<br>78<br>65 | 183–185 (dec.)<br>(CH₃COCH₃—H₂O) | 3328, 3196, 1671, 1636, 1608, 1375, 1249 1210 |
| 36 | —NH₂ | 2-OCOCH₃ | 5-OCH₃ | 1 | 61 | 141–144.5 | 3412, 3332, 1752, 1654, 1604, 1585, 1492, 1479, 1446, 1419, 1369, 1180 |
| 37 | —NH₂ | 4-OCOCH₃ | H | 11 | 76 | 195–198 (dec.)<br>(EtOH—H₂O) | 3380, 1732, 1654, 1240, 1201 |
| 38 | —NH₂ | 4-OCOOCH₂CH(CH₃)₂ | H | 11 | 27 | 154–155 | 3428, 1752, 1661, 1372, 1299, 1268, 1249, 1216, 750 |
| 39 | —NH₂ | 2-OCH₂CH(—O—)CH₂ | 5-OCH₃ | 15<br>16 | 26<br>80 | 187–189 | 3384, 3232, 3180, 1685, 1663, 1499, 1492, 1479, 1446, 1419, 1374, 1305, 1287, 1220, 1040 |
| 40*¹ | —NH₂ | 4-OCH₂CH(—O—)CH₂ | H | 15<br>16 | 82<br>85 | 176–179 | 3392, 3320, 1654, 1607, 1583, 1509, 1478, 1445, 1415, 1369, 1299, 1280, 1243, 1215, 1179, 749 |
| 41 | —N(CH₃)₂ | 2-OH | 5-OCH₃ | 13 | 64 | 186–188 | 3188, 1637, 1583, 1509, 1479, 1446, 1427, 1400, 1375, 1324, 1262, 1216, 1150, 750 |
| 42 | —N(CH₃)₂ | 4-OH | H | 13 | 74 | 210–211<br>(CH₃COCH₃—H₂O) | 3272, 2924, 2684, 2608, 2480, 2352, 2180, 1636, 1610, 1509, 1478, 1445, 1376, 1264, 1220 |
| 43 | —N(piperazinyl)—COOC₂H₅ | 4-OH | H | 13 | 64 | 156–161 (dec.) | 3308, 1647, 1593, 1513, 1474, 1433, 1374, 1280, 1222, 1171 |

TABLE 3-continued

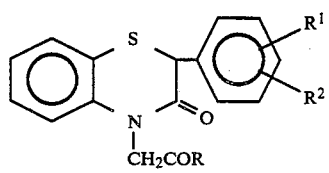

| Compound No. | R | R[1] | R[2] | Method (Example No.) | Yield (%) | mp (°C.) | IR (KBr, cm$^{-1}$) |
|---|---|---|---|---|---|---|---|
| 44 | —N⌒N—CH$_2$CH$_2$OH | 4-OH | H | 13<br>14 | 14<br>69 | 199.5-202.5<br>(EtOH—H$_2$O) | 3344, 1651, 1635, 1589, 1513, 1476, 1447, 1377, 1279, 1234 |
| 45 | —N⌒O | 4-OH | H | 13 | 48 | 263-265 (dec.) | 3200, 1646, 1629, 1585, 1474, 1467, 1444, 1267, 1230 |

*[1]Contains ¼ molecules of H$_2$O.

TABLE 4

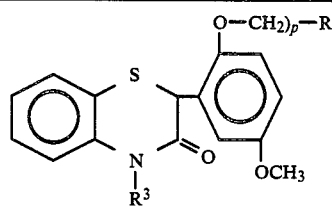

| Compound No. | R[3] | R | p | Method (Example No.) | Yield (%) | mp (°C.) | IR (KBr, cm$^{-1}$) |
|---|---|---|---|---|---|---|---|
| 46 | H | Cl | 3 | 17 | 43 | 116-119 | 3180, 1666, 1584, 1498, 1477, 1424, 1374, 1278, 1237, 1206, 1034, 749 680 |
| 47 | H | Br | 4 | 17<br>21 | 37<br>31 | 149-152 (dec.)<br>(C$_6$H$_4$—n-hexane) | 2944, 1664, 1582, 1498, 1474, 1424, 1364, 1270, 1238, 1205, 1042, 797, 746 |
| 48 | H | Br | 5 | 17 | 44 | 118-120 | 3180, 1672, 1585, 1501, 1480, 1367, 1241, 1211, 1040, 801, 751 |
| 49 | —CH$_3$ | Cl | 3 | 17<br>21 | 56<br>60 | 97,5-100 | 1646, 1581, 1467, 1424, 1354, 1271, 1234, 1203, 1147, 1044, 1019, 795, 750, 652 |
| 50 | —CH$_3$ | Br | 4 | 17 | 64 | 103-105 | 1655, 1586, 1496, 1472, 144,2 1427, 1363, 1273, 1238, 1204, 1154, 1044, 1020, 804, 765 |
| 51 | —CH$_3$ | Br | 5 | 17 | 61 | 92-94.5 | 1665, 1585, 1494, 1468, 1426, 1356, 1279, 1238, 1212, 1045m 1018, 743 |

TABLE 5

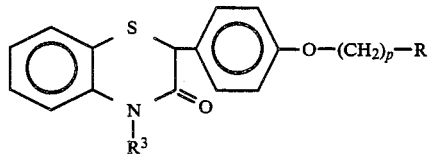

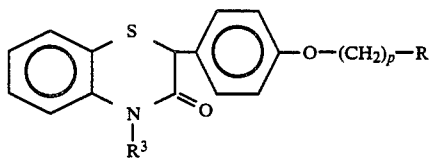

| Compound No. | R[3] | R | p | Method (Example No.) | Yield (%) | mp (°C.) | IR (KBr, cm$^{-1}$) |
|---|---|---|---|---|---|---|---|
| 52 | H | Cl | 3 | 17<br>21 | 44<br>41 | 175.5-178<br>(EtOH) | 3204, 3120, 2972, 1666, 1584, 1510, 1480, 1365, 1244, 749 |
| 53 | H | Cl | 6 | 17 | 45 | 160.5-162 | 3208, 1667, 1609, 1584, 1511, 1479, 1365, 1250, 1176, 800, 748 |
| 54 | —CH$_3$ | Cl | 3 | 17<br>21 | 40<br>53 | 97-99 | 1663, 1605, 1581, 1509, 1468, 1447, 1351, 1278, 1237, 1176, |

TABLE 5-continued

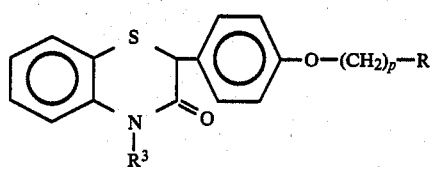

| Compound No. | R³ | R | p | Method (Example No.) | Yield (%) | mp (°C.) | IR (KBr, cm⁻¹) |
|---|---|---|---|---|---|---|---|

TABLE 6

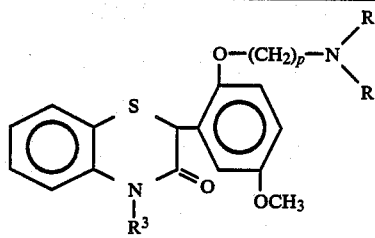

| Compound No. | R³ | R | R' | p | Method (Example No.) | Yield (%) | mp (°C.) | IR (KBr, cm⁻¹) |
|---|---|---|---|---|---|---|---|---|
| 55 | H | —CH₃ | —CH₃ | 3 | 18<br>19 | 37<br>67 | 136–137<br>(MeOH) | 1675, 1584, 1499, 1479, 1466, 1353, 1286, 1240, 1208, 1058, 809, 752 |
| 56 | H | —CH₃ | —⟨H⟩ | 3 | 19<br>20 | 69<br>76 | 136–137<br>(AcOEt) | 3180, 1665, 1584, 1499, 1479, 1375, 1237, 1206, 1047, 802, 752 |
| 57*¹ | H | —CH₃ | —⟨H⟩ | 4 | 19 | 53 | amorph. | 3384, 1663, 1582, 1493, 1473, 1232, 1034, 751, 718 |
| 58*² | H | —CH₃ | —⟨H⟩ | 5 | 19 | 94 | 146–147.5 (AcOEt) | 3410, 2470, 1671, 1593, 1551, 1498, 1476, 1375, 1351, 1239, 1204, 1036, 805, 715 |
| 59*³ | H | —CH₃ | —CH₂CH₂—⟨OCH₃, OCH₃⟩ | 3 | 19<br>20 | 38<br>57 | amorph. | 3420, 1719, 1671, 1583, 1501, 1474, 1235, 1025, 757 |
| 60*⁴ | H |  | ⟨cyclohexyl-CO-phenyl⟩ | 4 | 19<br>20 | 45<br>67 | 137–145 (dec.)<br>(EtOH—AcOEt) | 3400, 3170, 2640, 2500, 1674, 1581, 1500, 1478, 1368, 1273, 1238, 1216, 1038, 976, 754, 699 |
| 61 | —CH₃ | —CH₃ | —CH₃ | 3 | 18<br>19<br>20 | 51<br>62<br>74 | 82–84<br>(EEt₂O) | 1655, 1582, 1498, 1458, 1444, 1356, 1306, 1240, 1216, 1145, 1037, 809, 741 |
| 62*¹ | —CH₃ | —CH₃ | —⟨H⟩ | 3 | 19<br>20 | 52<br>77 | 116–120 (dec.)<br>(EtOH) | 1653, 1465, 1353, 1272, 1237, 1205, 1152, 1039, 752, 704 |
| 63*¹ | —CH₃ | —CH₃ | —⟨H⟩ | 4 | 19 | 78 | 150–151.5 (dec.)<br>(EtOH) | 3420, 2650, 1663, 1584, 1499, 1468, 1357, 1275, 1238, 1208, 1037, 756 |
| 64*¹ | —CH₃ | —CH₃ | —⟨H⟩ | 5 | 19 | 65 | amorph. | 3376, 2630, 1702, 1653, 1581, 1455, 1203, 1033, 932, 807, 750, 716 |
| 65*¹ | —CH₃ | —CH₃ | ⟨cyclohexyl-CO-phenyl⟩ | 4 | 20 | 62 | 173–175 (dec.)<br>(EtOH—H₂O) | 3425, 2650, 1510, 1669, 1584, 1500, 1473, 1446, 1354, 1277, 1238, 1217, 1038, 701 |

TABLE 6-continued

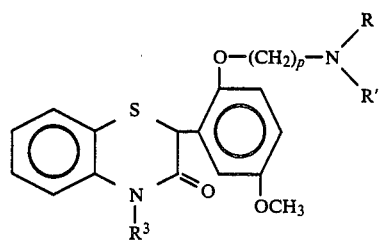

| Compound No. | R³ | R | R' | p | Method (Example No.) | Yield (%) | mp (°C.) | IR (KBr, cm⁻¹) |
|---|---|---|---|---|---|---|---|---|
| 66 | —CH₃ | | cyclohexyl-CO-C₆H₄-F (4-F) | 4 | 19 | 22 | 135-138 (CHCl₃—iso-Pr₂O) | 1660, 1592, 1499, 1277, 1183 |
| | | | | | 20 | 41 | | |

*¹oxalic acid - salt
*²benzoic acid - salt
*³citric acid - salt
*⁴fumaric acid - salt

TABLE 7

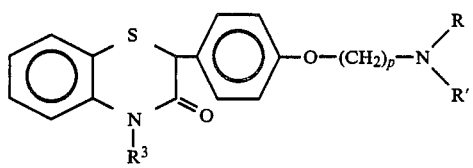

| Compound No. | R³ | R | R' | p | Method (Example No.) | Yield (%) | mp (°C.) | IR (KBr, cm⁻¹) |
|---|---|---|---|---|---|---|---|---|
| 67*¹ | H | —CH₃ | —CH₃ | 3 | 18 | 45 | 202-206 (dec.) (EtOH) | 3420, 2660, 1670, 1578, 1475, 1350, 1243, 1229, 1173, 752, 645 |
| | | | | | 19 | 68 | | |
| 68 | H | —CH₃ | cyclohexyl | 3 | 19 | 57 | 130-133 (EtOH) | 3060, 2848, 1675, 1583, 1511, 1482, 1369, 1245, 743 |
| 69 | H | —CH₃ | cyclohexyl | 6 | 19 | 73 | 131-132.5 (AcOEt) | 3208, 1670, 1609, 1583, 1511, 1482, 1368, 1242, 1178, 799, 747 |
| 70*¹ | H | | cyclohexyl-CH₂-C₆H₅ | 3 | 20 | 58 | 181-184 (dec.) (EtOH) | 3044, 1675, 1605, 1581, 1509, 1478, 1378, 1299, 1240, 748 |
| 71*² | H | | piperidino-N—CH₂CH₂—C₆H₃(OCH₃)₂ | 3 | 20 | 41 | 238-241 (dec.) (EtOH) | 2932, 2488, 1666, 1606, 1583, 1510, 1378, 1299, 1240, 748 |
| 72 | —CH₃ | —CH₃ | —CH₃ | 3 | 18 | 38 | 99.5-101 (Et₂O) | 1665, 1608, 1582, 1510, 1474, 1353, 1240, 1177, 1050, 765 |
| | | | | | 20 | 71 | | |
| 73*¹ | —CH₃ | —CH₃ | cyclohexyl | 3 | 19 | 60 | 149-150.5 (EtOH) | 3420, 2610, 1702, 1654, 1608, 1582, 1510, 1467, 1356, 1247, 1175, 980, 746, 643 |

*¹fumaric acid - salt
*²dihydrochloride

TABLE 8

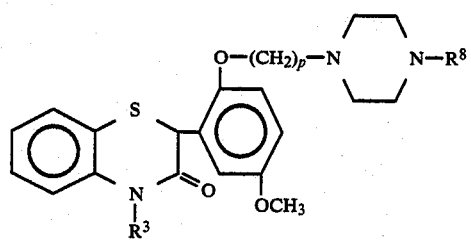

| Compound No. | R³ | R⁸ | p | Method (Example No.) | Yield (%) | mp (°C.) | IR (KBr, cm⁻¹) |
|---|---|---|---|---|---|---|---|
| 74*1 | H | —CH₂CH₂—(3,4,5-triOCH₃-phenyl) | 3 | 20 | 64 | 231–232 (dec.) (EtOH) | 3412, 2530, 1663, 1587, 1500, 1458, 1424, 1239, 1122, 747 |
| 75*2 | H | —CH₂CH₂—(3,4,5-triOCH₃-phenyl) | 4 | 20 | 61 | 181–183 (dec.) (EtOH—CH₃CN) | 3410, 1671, 1586, 1500, 1458, 1419, 1349, 1122, 1034, 975, 748, 633 |
| 76*3 | H | —CH₂CO—phenyl | 3 | 20 | 58 | 147–148 (EtOH) | 3420, 2540, 1671, 1577, 1499, 1477, 1357, 1235, 1212, 1040, 863, 751 |
| 77*1 | —CH₃ | —CH₂CH₂—(3,4,5-triOCH₃-phenyl) | 3 | 20 | 72 | 210–213 (EtOH) | 3428, 2932, 2360, 1663, 1558, 1499, 1462, 1424, 1356, 1243, 1205, 1117, 1029, 1005, 748 |
| 78*1 | —CH₃ | —CH₂CH₂—(3,4,5-triOCH₃-phenyl) | 4 | 19, 20 | 54, 84 | 195.5–197.5 (dec.) (EtOH) | 3404, 2928, 2380, 1645, 1586, 1499, 1464, 1425, 1241, 1121, 1038, 761 |
| 79*1 | —CH₃ | —CH₂CO—phenyl | 4 | 20 | 69 | 210–212 (EtOH—H₂O) | 2400, 1685, 1660, 1583, 1499, 1466, 1446, 1356, 1278, 1236, 1215, 1036, 947, 752 |

*1 dihydrochloride
*2 di-fumaric acid - salt
*3 di-maleic acid - salt

TABLE 9

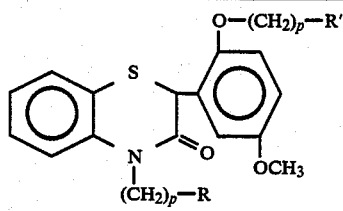

| Compound No. | R | R' | p | Method (Example No.) | Yield (%) | mp (°C.) | IR (KBr, cm⁻¹) |
|---|---|---|---|---|---|---|---|
| 80 | Br | Br | 5 | 22 | 74 | oil | 1668, 1588, 1502, 1480, 1449, 1379, 1279, 1241, 1222, 1043, 752 (neat) |
| 81 | —N(CH₃)₂ | Cl | 3 | 17 | 46 | oil | 2940, 1663, 1585, 1500, 1478, 1466, 1445, 1375, 1307, 1277, 1240, 1218, 1042, 749 (neat) |
| 82*1 | —N(CH₃)₂ | —N(CH₃)₂ | 3 | 18, 23, 24, 29 | 59, 57, 66, 87 | 185.5–186.5 (dec.) (MeOH—H₂O) | 3420, 2650, 1717, 1653, 1583, 1500, 1471, 1442, 1399, 1277, 1213, 1156, 1040, 717, 493 |

TABLE 9-continued

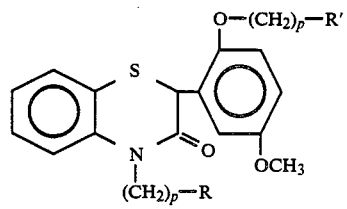

| Compound No. | R | R' | p | Method (Example No.) | Yield (%) | mp (°C.) | IR (KBr, cm$^{-1}$) |
|---|---|---|---|---|---|---|---|
| 83 | -N(piperidinyl-CH₃) | -N(piperidinyl-CH₃) | 3 | 19 | 38 | oil | 2928, 2852, 1666, 1500, 1479, 1446, 1372, 1278, 1240, 1219, 1045, 750 |
| 84*2 | —N(CH₃)₂ | —N(CH₃)₂ | 5 | 20 | 47 | amorph. | 2916, 1717, 1202, 1184, 1178 |
|  |  |  |  | 24 | 41 |  |  |
| 85*2 | -N(piperidinyl-CH₃) | -N(piperidinyl-CH₃) | 5 | 19 | 42 | amorph. | 2928, 1718, 1654, 1442, 1375, 1231, 1206 |

*¹di-oxalic acid - salt
*²di-citric acid - salt

TABLE 10

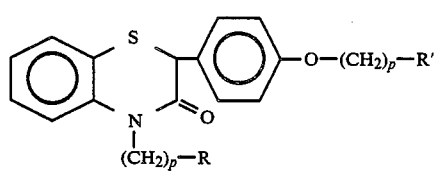

| Compound No. | R | R' | p | Method (Example No.) | Yield (%) | mp (°C.) | IR (KBr, cm$^{-1}$) |
|---|---|---|---|---|---|---|---|
| 86 | Cl | Cl | 3 | 22 | 79 | 93-96 | 2920, 1663, 1610, 1510, 1477, 1437, 1375, 1249, 1180, 790, 757 |
| 87 | Cl | Cl | 6 | 22 | 70 | oil | 1664, 1610, 1584, 1510, 1376, 1356, 1303, 1249, 1175, 751, 645 (neat) |
| 88 | —N(CH₃)₂ | Cl | 3 | 21 | 50 | oil | 2936, 1660, 1608, 1583, 1510, 1477, 1445, 1375, 1301, 1277, 1246, 1176, 749 (neat) |
| 89*1 | —N(CH₃)₂ | —N(CH₃)₂ | 3 | 18 | 55 | amorph. | 1718, 1653, 1604, 1577, 1509, 1473, 1437, 1375, 1300, 1225, 1174 |
|  |  |  |  | 23 | 49 |  |  |
|  |  |  |  | 24 | 63 |  |  |
| 90*1 | -N(piperidinyl-CH₃) | -N(piperidinyl-CH₃) | 3 | 20 | 56 | amorph. | 2928, 1722, 1655, 1604, 1577, 1509, 1473, 1442, 1374, 1300, 1236 |
| 91*2 | -N(piperidinyl-CH₃) | -N(piperidinyl-CH₃) | 6 | 19 | 37 | amorph. | 2924, 2856, 1701, 1685, 1654, 1374, 1239, 1172, 979, 747, 643 |
|  |  |  |  | 20 | 59 |  |  |

*¹di-citric acid - salt
*²fumaric acid - salt

TABLE 11

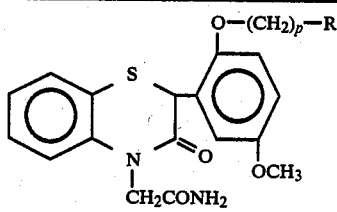

| Compound No. | R | p | Method (Example No.) | Yield (%) | mp (°C.) | IR KBr, cm⁻¹) |
|---|---|---|---|---|---|---|
| 92 | Cl | 3 | 21 | 82 | 158–162 | 1650, 1585m 1499m 1479, 1446, 1419, 1374, 1300, 1284, 1264, 1241m 1219, 1038, 750 |
| 93 | —N(CH₃)₂ | 3 | 18<br>20<br>25 | 61<br>75<br>80 | 159–162<br>(CH₃COCH₃) | 3416, 3320, 2932, 1684, 1647, 1584, 1499, 1478, 1465, 1447, 1419, 1375, 1300, 1283, 1264, 1241, 1220, 750 |
| 94* | —N⟨piperidine⟩-CH₃ | 3 | 19<br>25 | 48<br>74 | 62–66 (dec.)<br>(CH₃COCH₃) | 3324, 3180, 2916, 2848, 1657, 1584, 1498, 1478, 1445, 1418, 1372, 1299, 1285, 1264, 1239, 1218, 1038 |

*Contains 2 molecules of acetone.

TABLE 12

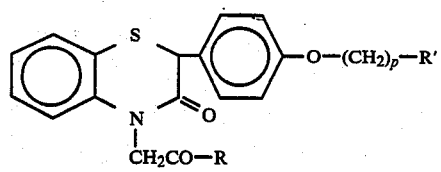

| Compound No. | R | R' | p | Method (Example No.) | Yield (%) | mp (°C.) | IR (KBR, cm⁻¹) |
|---|---|---|---|---|---|---|---|
| 95 | —NH₂ | Cl | 3 | 21 | 46 | 200–204 | 3392, 1657, 1617, 1608, 1577, 1477, 1368, 1302, 1247, 1208, 748 |
| 96 | —NH₂ | —N(CH₃)₂ | 3 | 20<br>25 | 49<br>48 | 134–136<br>(CH₃COCH₃—H₂O) | 3384, 3324, 3180, 2932, 1657, 1607, 1582, 1509, 1477, 1444, 1419, 1370, 1299, 1280, 1244, 1212, 1175, 748 |
| 97 | —NH₂ | —N⟨piperidine⟩-CH₃ | 3 | 20<br>25 | 66<br>62 | 143–146 (dec.)<br>(CH₃COCH₃) | 3384, 3320, 2920, 2848, 1655, 1608, 1583, 1509, 1478, 1445, 1419, 1370, 1299, 1281, 1245, 1215, 1175 |
| 98 | —N(CH₃)₂ | Cl | 3 | 21 | 64 | 118–121 | 1654, 1607, 1582, 1509, 1478, 1445, 1420, 1396, 1376, 1320, 1242, 1177, 1146, 762, 748 |
| 99*¹ | —N(CH₃)₂ | —N(CH₃)₂ | 3 | 18<br>25 | 37<br>50 | 168–169.5<br>(CH₃COCH₃—MeOH) | 3412, 1648, 1602, 1577, 1478, 1379, 1363, 1237, 1178, 984 |
| 100 | —N(CH₃)₂ | —N⟨piperazine⟩N—CH₂CO—⟨phenyl⟩ | 3 | 20 | 35 | 148–151.5 (dec.)<br>(EtOH) | 2920, 2796, 1654, 1606, 1578, 1509, 1478, 1446, 1375, 1316, 1285, 1243, 1170 |
| 101 | —N⟨morpholine⟩ | Cl | 3 | 21 | 74 | amorph. | 1654, 1607, 1509, 1477, 1445, 1376, 1235, 1175, 1110, 1030, 749 |
| 102*² | —N⟨morpholine⟩ | —N(CH₃)₂ | 3 | 18<br>25 | 29<br>51 | 188–200.5 (dec.)<br>(EtOH—H₂O) | 3400, 1647, 1607, 1577, 1510, 1473, 1446, 1377, 1235 |

TABLE 12-continued

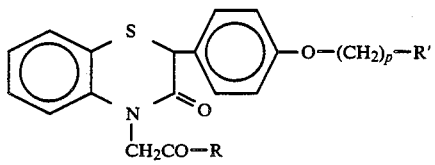

| Compound No. | R | R' | p | Method (Example No.) | Yield (%) | mp (°C.) | IR (KBR, cm$^{-1}$) |
|---|---|---|---|---|---|---|---|
| 103 | —N⌒N—COOC$_2$H$_5$ | Cl | 3 | 21 | 88 | 94–96 | 1655, 1608, 1509, 1473, 1465, 1458, 1430, 1376, 1283, 1227, 1174, 1026 |
| 104 | —N⌒N—COOC$_2$H$_5$ | —N⌒—CO—⌬—F | 3 | 20, 26 | 31, 66 | amorph. | 1658, 1594, 1509, 1444, 1428, 1225 |

*[1] maleic acid - salt
*[2] fumaric acid - salt

TABLE 13

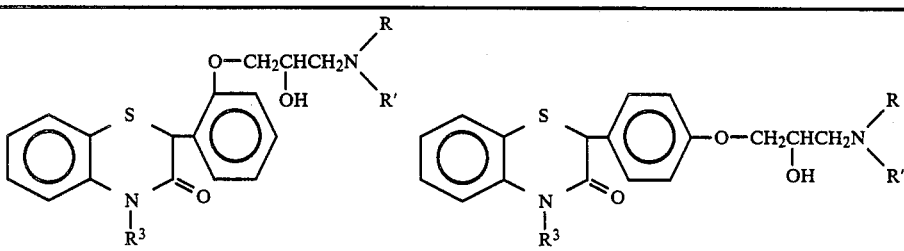

Compound No. 105–108            Compound No. 109–110

| Compound No. | R$^3$ | R | R' | Method (Example No.) | Yield (%) | mp (°C.) | IR (KBr, cm$^{-1}$) |
|---|---|---|---|---|---|---|---|
| 105 | H | H | —C(CH$_3$)$_3$ | 27 | 93 | 182–183 (EtOH—CH$_2$Cl$_2$) | 3400, 3256, 1669, 1584, 1500, 1479, 1359, 1238, 1213, 1041, 745 |
| 106*[1] | —CH$_3$ | H | —C(CH$_3$)$_3$ | 27 | 84 | 187–188 (EtOH—H$_2$O) | 3364, 1664, 1560, 1499, 1380, 1353, 1281, 1240, 1213, 1128, 1041, 748 |
| 107*[2] | —CH$_3$ | ⌒N—CH$_2$CO—⌬ | | 27, 28 | 28, 84 | 145–146 (dec.) (EtOH—H$_2$O) | 3380, 2430, 1691, 1653, 1617, 1576, 1493, 1355, 1235, 1212, 1037, 864, 750 |
| 108 | —CH$_2$CONH$_2$ | H | —C(CH$_3$)$_3$ | 27 | 68 | 202–204 (dec.) (CH$_3$COCH$_3$—H$_2$O) | 3332, 3172, 2944, 1658, 1585, 1499, 1478, 1458, 1446, 1418, 1399, 1365, 1302, 1282, 1264, 1241, 1220, 1034, 747 |
| 109*[3] | —(CH$_2$)$_3$N(CH$_3$)$_2$ | H | —C(CH$_3$)$_3$ | 27 | 48 | amorph. | 3368, 2936, 1700, 1637, 1602, 1578, 1437, 1375, 1315, 1309, 1232 |
| 110 | —CH$_2$CONH$_2$ | H | —C(CH$_3$)$_3$ | 27 | 82 | amorph. | 3320, 3212, 3184, 3060, 2592, 1661, 1657, 1607, 1583, 1509, 1478, 1446, 1369, 1299, 1244, 1215 |

*[1] ½-succinic acid - salt
*[2] di-maleic acid - salt
*[3] di-citric acid - salt, contains 1 molecules of ethyl acetate

Pharmacological Activities

Calcium antagonists have not only potentially beneficial effects in the treatment of many diseases but also serve as valuable research tools to elucidate excitation-contraction coupling in various muscle types (A. Fleckenstein, Ann. Rev. Pharmacol., 17, 149–166, 1977). Therefore, we examined the calcium-antagonistic activity of the compounds of this invention.

Pharmacological test I

The action potentials on the smooth muscles of uterus, teania coli and portal vein are dependent on calcium ion, and therefor these smooth muscle preparations are useful for screening of calcium antagonists. We measured the calcium-antagonistic activity of the compounds by the method using guinea-pig teania coli preparation.

Isolated guinea-pig teania coli was suspended in a 20 ml organ bath with Krebs solution at 32° C. and bubbled with 5% carbon dioxide in oxygen. After equilibration, the muscle was washed with Ca$^{++}$-free Krebs solution, and when the muscle had relaxed to basal level, it was suspended in Ca$^{++}$-free-high-K Krebs solution.

The muscle was exposed to test compounds for 5 minutes before addition of $CaCl_2$, and the contraction evoked by $CaCl_2 (3 \times 10^{-4} M)$ was recorded isotonically. The calcium-antagonistic activity was represented by the concentration of test compound which elicited 50% inhibition of $Ca^{++}$-evoked contraction ($IC_{50}$).

As shown in Table 14, the compounds of this invention had calcium-antagonistic activity.

Blood platelet plays an important role not only in hemostasis but also in thrombosis. Platelet hyperaggregability leads to an increase in the number of circulating platelet aggregates, which may contribute toward the development of cardiac arrythmias, cardiac arrest or myocardial infarction. These cardiovascular diseases can be prevented by inhibition of platelet aggregation. Therefore, we screened the influence of test compounds on platelet aggregation in vitro, and found that they have anti-aggregatory activity.

Pharmacological test II

Blood was obtained from an anesthetized rabbit using 0.1 volumes of 3.8% sodium citrate as anticoagulant. Platelet rich plasma(PRP) was isolated by centrifugation at 650 rpm for 10 minutes at room temperature. After preincubation of PRP (0.25 ml) with various concentrations of test compounds (14 μl) for 1 minute at 37° C., collagen (3 μg/ml:final concentration) or ADP (3 μM:final concentration) was added to induce aggregation and the aggregation profiles were monitored with RIKADENKI six-channel aggregometer. The control experiment contained saline instead of test compound.

The anti-aggregatory activity was represented by the concentration of test compound which elicited 50% inhibition of control response.

As shown in the Table 15, the compounds of this invention had anti-aggregatory activity.

TABLE 14

| Calcium-antagonistic activity | |
|---|---|
| Compound No. | $IC_{50}$ [M] |
| 58 | $2.6 \times 10^{-6}$ |
| 59 | $2.0 \times 10^{-6}$ |
| 61 | $2.5 \times 10^{-6}$ |
| 62 | $1.6 \times 10^{-6}$ |
| 64 | $3.0 \times 10^{-6}$ |
| 65 | $1.8 \times 10^{-6}$ |
| 68 | $1.9 \times 10^{-6}$ |
| 71 | $2.0 \times 10^{-6}$ |
| 72 | $2.6 \times 10^{-6}$ |
| 73 | $3.4 \times 10^{-6}$ |
| 75 | $3.0 \times 10^{-6}$ |
| 77 | $1.6 \times 10^{-6}$ |
| 79 | $3.9 \times 10^{-6}$ |
| 107 | $3.8 \times 10^{-6}$ |

TABLE 15

| Anti-aggregatory activity | |
|---|---|
| Compound No. | $IC_{50}$ [M] |
| 55 | $3.2 \times 10^{-6}$ |
| 57 | $3.2 \times 10^{-6}$ |
| 63 | $3.2 \times 10^{-6}$ |
| 67 | $1.6 \times 10^{-6}$ |
| 76 | $3.2 \times 10^{-6}$ |
| 78 | $3.5 \times 10^{-6}$ |
| 82 | $3.2 \times 10^{-6}$ |
| 105 | $1.0 \times 10^{-6}$ |
| 106 | $1.3 \times 10^{-6}$ |

Toxicity test

Acute toxicity of the compounds of this invention is shown in Table 16. (animal)

Male ddy-SLC strain mice (4 weeks of age, weighing 19-21 g) were placed in a breeding room of constant temperature and humidity (23±1° C., 55±5%) and fed freely pellet diet and water ad. libitum for a week. Mice showing normal growth were selected for the test. (method of administration)

Test compounds are suspended in 0.5% tragacanth suspension and administered orally in a dose of 0.5 ml/20 g body weight.

TABLE 16

| Compound No. | $LD_{50}$ (mg/Kg) |
|---|---|
| 73 | 500–1000 |
| 77 | >1280 |

The compounds can be administered either orally or parenterally. The dosage forms are tablet, capsule, granule, powder, suppository, injection, etc. The dose is adjusted depending on symptom, dosage form, etc., but usual daily dosage is 1 to 5,000 mg, preferably 10 to 1,000 mg, in one or a few divided doses.

Examples of formulation are shown below.

| Example of formulation | | |
|---|---|---|
| (a) tablet | | |
| compound No. 55 | | 30 mg |
| lactose | | 150 mg |
| crystalline cellulose | | 50 mg |
| calcium carboxymethylcellulose | | 7 mg |
| magnesium stearate | | 3 mg |
| | total | 240 mg |
| compound No. 62 | | 50 mg |
| lactose | | 120 mg |
| crystalline cellulose | | 60 mg |
| calcium carboxymethylcellulose | | 7 mg |
| magnesium stearate | | 3 mg |
| | total | 240 mg |
| compound No. 65 | | 60 mg |
| lactose | | 120 mg |
| crystalline cellulose | | 60 mg |
| calcium carboxymethylcellulose | | 7 mg |
| magnesium stearate | | 3 mg |
| | total | 250 mg |
| compound No. 67 | | 40 mg |
| lactose | | 150 mg |
| crystalline cellulose | | 50 mg |
| calcium carboxymethylcellulose | | 7 mg |
| magnesium stearate | | 3 mg |
| | total | 250 mg |
| compound No. 68 | | 70 mg |
| lactose | | 110 mg |
| crystalline cellulose | | 60 mg |
| calcium carboxymethylcellulose | | 7 mg |
| magnesium stearate | | 3 mg |
| | total | 250 mg |

The tablets may be treated with the common film-coating and further with sugar-coating.

| | | |
|---|---|---|
| (b) granule | | |
| compound No. 73 | | 30 mg |
| polyvinylpyrrolidone | | 25 mg |
| lactose | | 385 mg |
| hydroxypropylcellulose | | 50 mg |
| talc | | 10 mg |
| | total | 500 mg |
| compound No. 77 | | 50 mg |
| polyvinylpyrrolidone | | 25 mg |
| lactose | | 365 mg |

| | | |
|---|---:|---:|
| hydroxypropylcellulose | 50 | mg |
| talc | 10 | mg |
| total | 500 | mg |
| (c) powder | | |
| compound No. 82 | 30 | mg |
| lactose | 500 | mg |
| starch | 440 | mg |
| colloidal silica | 30 | mg |
| total | 1000 | mg |
| compound No. 105 | 50 | mg |
| lactose | 480 | mg |
| starch | 440 | mg |
| colloidal silica | 30 | mg |
| total | 1000 | mg |
| (d) capsule | | |
| compound No. 106 | 30 | mg |
| lactose | 102 | mg |
| crystalline cellulose | 56 | mg |
| colloidal silica | 2 | mg |
| total | 190 | mg |
| compound No. 107 | 50 | mg |
| glycerol | 329.8 | mg |
| butyl p-hydroxybenzoate | 0.02 | mg |
| total | 380 | mg |

What we claim is:

1. A compound of the formula or a salt thereof,

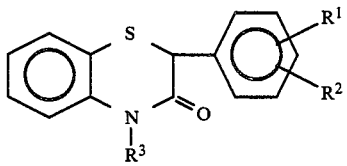 [I]

wherein
$R^1$ is

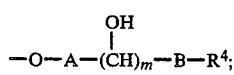

$-O-A-(CH)_m-B-R^4$;

$R^2$ is selected from the group consisting of hydrogen, $(C_1-C_6)$alkyl, halogen, nitro, hydroxy, amino, $(C_1-C_6)$alkoxy, $(C_1-C_6)$alkanoyloxy, $(C_1-C_6)$alkylamino and $(C_1-C_6)$alkoxycarbonyloxy;

$R^3$ is hydrogen, $(C_1-C_6)$alkyl or

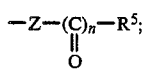

$-Z-(C)_n-R^5$;
    ‖
    O $R^4$ and $R^5$ are same or different and are selected from the group consisting of hydroxy, halogen, methoxy

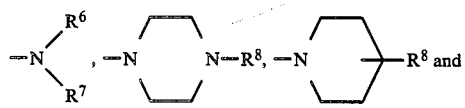,

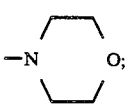;

$R^6$ and $R^7$ are same or different and are selected from the group consisting of hydrogen, $(C_1-C_6)$alkyl, $(C_4-C_7)$cycloalkyl and phenyl-$(C_1-C_6)$alkyl, and said phenyl nucleus can be substituted by hydroxy, $(C_1-C_6)$alkyl or $(C_1-C_6)$alkoxy;

$R^8$ is selected from the group consisting of hydrogen, $(C_1-C_6)$alkyl, $(C_1-C_6)$alkanoyl, $(C_1-C_6)$alkoxycarbonyl, carboxy, phenyl, phenylcarbonyl, phenyl-$(C_1-C_6)$alkyl, phenyl-$(C_1-C_6)$alkanoyl, and phenylcarbonyl-$(C_1-C_6)$alkyl, and said alkyl and alkanoyl groups can be substituted by hydroxy, $(C_1-C_6)$alkoxy, carboxy, $(C_1-C_6)$alkoxycarbonyl, halogen, amino, $(C_1-C_6)$alkylamino or tetrahydropyranyloxy, and said phenyl nucleus can be substituted by $(C_1-C_6)$alkyl, hydroxy, $(C_1-C_6)$alkoxy, $(C_1-C_6)$alkanoyl, $(C_1-C_6)$alkoxycarbonyl, halogen, amino or $(C_1-C_6)$alkylamino;

A, B and Z are same or different and are $(C_1-C_6)$alkylene; and m and n each is 0 or 1.

2. The compound as in claim 1, wherein m is 1.

3. The compound as in claim 1, wherein m is 0.

4. The compound as in claim 1, wherein $R^1$ is hydroxy, methoxy, acetyloxy, tetrahydropyranyloxy, isobutyloxycarbonyloxy or dimethylamino.

5. The compound as in claim 1, wherein $R^2$ is hydrogen, methyl, methoxy, hydroxy, chloro or nitro.

6. The compound as in claim 1, wherein $R^3$ is hydrogen or methyl.

7. The compound as in claim 1, wherein $R^4$ is chloro or bromo.

8. The compound as in claim 1, wherein $R^3$ is $-Z-(C)_n-R^5$
    ‖
    O and $R^5$ is chloro, bromo, hydroxy, methoxy, amino or dimethylamino.

9. The compound as in claim 1, wherein at least one of $R^4$ and $R^5$ is

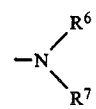

and $R^6$ and $R^7$ each is hydrogen, methyl, cyclohexyl, tert-butyl or 3,4-dimethoxyphenethyl.

10. The compound as in claim 1, wherein at least one of $R^4$ and $R^5$ is

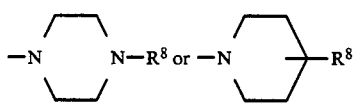

and $R^8$ is ethoxycarbonyl, hydroxyethyl, benzoyl, benzyl, 4-fluorobenzoyl, benzoylmethyl, 3,4-dimethoxyphenethyl or 3,4,5-trimethoxyphenethyl.

11. The compound as in claim 1, wherein $R^4$ is selected from the group consisting of hydrogen, halogen,

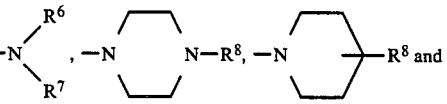

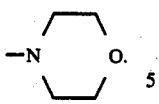

12. The compound as in claim 1, wherein all halogens specified therein are selected from the group consisting of chloro, bromo and fluoro.

13. The compound as in claim 2, wherein A and B are —CH$_2$—.

14. A compound of the formula [I] or a salt thereof,

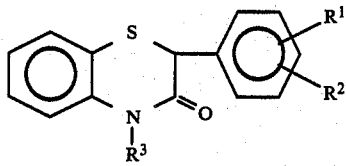

wherein
R$^1$ is

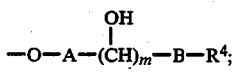

R$^2$ is hydrogen or methoxy;
R$^3$ is hydrogen or methyl;
R$^4$ is selected from the group consisting of chlorine, bromine,

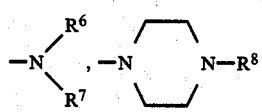

and piperidine which can be substituted by benzyl, phenylcarbonyl or (fluorophenyl)carbonyl;
R$^6$ and R$^7$ are same or different and are selected from the group consisting of hydrogen, methyl, cyclohexyl and phenethyl which can be substituted by one or more methoxy group(s);
R$^8$ is phenethyl which can be substituted by one or more methoxy group(s) or phenylcarbonylmethyl;
A and B are same or different and are (C$_1$–C$_6$)alkylene; and
m is 0.

15. 3,4-Dihydro-2-[2-(3-dimethylaminopropoxy)-5-methoxyphenyl]-3-oxo-2H-1,4-benzothiazine as in claim 14.

16. 3,4-Dihydro-2-[5-methoxy-2-[3-(N-methylcyclohexylamino)propoxy]-4-methyl-3-oxo-2H-1,4-benzothiazine as in claim 14.

17. 3,4-Dihydro-2-[5-methoxy-2-[4-(N-methylcyclohexylamino)butoxy]phenyl]-4-methyl-3-oxo-2H-1,4-benzothiazine as in claim 14.

18. 2-[2-[4-(4-Benzoylpiperidino)butoxy]-5-methoxyphenyl]-3,4-dihydro-4-methyl-3-oxo-2H-1,4-benzothiazine as in claim 14.

19. 3,4-Dihydro-2-[4-(3-dimethylaminopropoxy)phenyl]-3-oxo-2H-1,4-benzothiazine as in claim 14.

20. 3,4-Dihydro-2-[4-[3-(N-methylcyclohexylamino)propoxy]phenyl]-3-oxo-2H-1,4-benzothiazine as in claim 14.

21. 3,4-Dihydro-2-[5-methoxy-2-[4-[4-(3,4,5-trimethoxyphenethyl)piperazino]butoxy]phenyl]-4-methyl-3-oxo-2H-1,4-benzothiazine as in claim 14.

22. A compound of the formula [I] or a salt thereof,

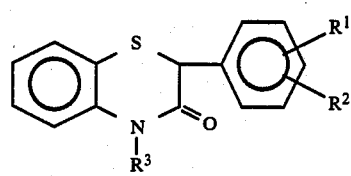

wherein
R$^1$ is

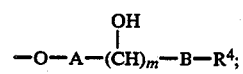

R$^2$ is hydrogen or methoxy;
R$^3$ is

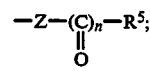

R$^4$ is chlorine, bromine,

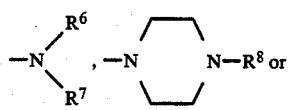

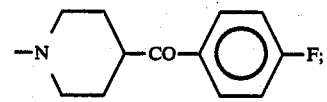

R$^5$ is chlorine, bromine, hydroxy,

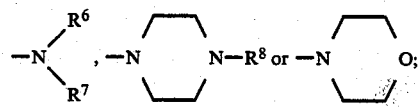

R$^6$ and R$^7$ are same or different and are hydrogen, methyl or cyclohexyl;
R$^8$ is phenylcarbonylmethyl or ethoxycarbonyl;
A and B are same or different and are (C$_1$–C$_6$)alkylene;
Z is (C$_1$–C$_6$)alkylene;
m is 0; and
n is 0 or 1.

23. 3,4-Dihydro-2-[2-(3-dimethylaminopropoxy)-5-methoxyphenyl]-4-(3-dimethylaminopropyl)-3-oxo-2H-1,4-benzothiazine as in claim 22.

24. A compound of the formula [I] or a salt thereof,

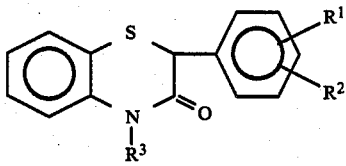

wherein $R^1$ is

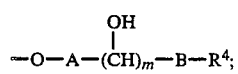

$R^2$ is hydrogen or methoxy;

$R^3$ is hydrogen, methyl or

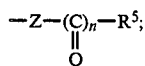

$R^4$ is

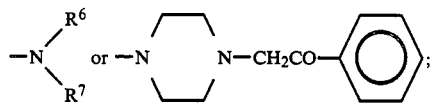

$R^5$ is hydroxy, amino or dimethylamino;

$R^6$ and $R^7$ are same or different and are hydrogen or $-C(CH_3)_3-$;

Z is $(C_1-C_3)$alkylene;

m is 1; and n is 0 or 1.

25. 2-[2-(3-tert-Butylamino-2-hydroxypropoxy)-5-methoxyphenyl]-3,4-dihydro-3-oxo-2H-1,4-benzothiazine as in claim 24.

26. 3,4-Dihydro-2-[2-[2-hydroxy-3-(4-phenacyl-piperazino)propoxy]-5-methoxyphenyl]-4-methyl-3-oxo-2H-1,4-benzothiazine as in claim 24.

27. A compound of the formula [I] or a salt thereof,

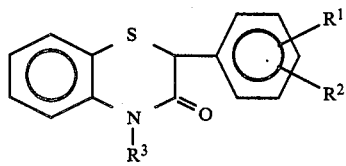

wherein $R^1$ is selected from the group consisting of hydrogen, hydroxy, $(C_1-C_6)$alkoxy, $(C_1-C_6)$alkanoyloxy, $(C_1-C_6)$alkoxycarbonyloxy, tetrahydropyranyloxy, amino, and $(C_1-C_6)$alkylamino;

$R^2$ is selected from the group consisting of hydrogen, $(C_1-C_6)$alkyl, nitro, hydroxy, amino, $(C_1-C_6)$alkoxy, $(C_1-C_6)$alkanoyloxy, $(C_1-C_6)$alkylamino and $(C_1-C_6)$ alkoxycarbonyloxy;

$R^3$ is $(C_1-C_6)$alkyl or

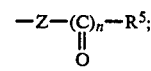

$R^5$ is selected from the group consisting of hydroxy, halogen, methoxy,

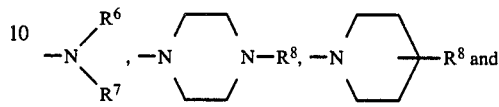

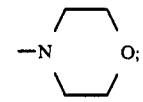

$R^6$ and $R^7$ are same or different and are selected from the group consisting of hydrogen, $(C_1-C_6)$alkyl, $(C_4-C_7)$cycloalkyl and phenyl-$(C_1-C_6)$alkyl, and said phenyl nucleus can be substituted by hydroxy, $(C_1-C_6)$alkyl or $(C_1-C_6)$alkoxy;

$R^8$ is selected from the group consisting of hydrogen, $(C_1-C_6)$alkyl, $(C_1-C_6)$alkanoyl, $(C_1-C_6)$alkoxycarbonyl, carboxy, phenyl, phenylcarbonyl, phenyl-$(C_1-C_6)$alkyl, phenyl-$(C_1-C_6)$alkanoyl, and phenylcarbonyl-$(C_1-C_6)$alkyl, and said alkyl and alkanoyl groups can be substituted by hydroxy, $(C_1-C_6)$alkoxy, carboxy, $(C_1-C_6)$alkoxycarbonyl, halogen, amino, $(C_1-C_6)$alkylamino or tetrahydropyranyloxy, and said phenyl nucleus can be substituted by $(C_1-C_6)$alkyl, hydroxy, $(C_1-C_6)$alkoxy, $(C_1-C_6)$alkanoyl, $(C_1-C_6)$alkoxycarbonyl, halogen, amino or $(C_1-C_6)$alkylamino;

A, B and Z are same or different and are $(C_1-C_6)$alkylene; and n is 0 or 1.

28. A pharmaceutical composition having a platelet anti-aggregation effect comprising (i) a pharmaceutical carrier and (ii) a platelet anti-aggregative effective amount of a compound of claim 1.

29. A method of preventing the aggregation of platelets comprising administering the composition of claim 28 in a platelet anti-aggregative effective amount.

30. A pharmaceutical composition having a platelet anti-aggregation effect comprising (i) a pharmaceutical carrier and (ii) a platelet anti-aggregative effective amount of a compound of claim 27.

31. A method of preventing the aggregation of platelets comprising administering the composition of claim 30 in a platelet anti-aggregative effective amount.

32. A method of lowering excessive calcium blood levels comprising administering a compound of claim 1 in an amount sufficient to lower excessive calcium blood levels.

* * * * *

UNITED STATES PATENT AND TRADEMARK OFFICE
CERTIFICATE OF CORRECTION

PATENT NO. : 4,584,300

DATED : April 22, 1986

INVENTOR(S) : IWAO et al

Page 1 of 4

It is certified that error appears in the above-identified patent and that said Letters Patent is hereby corrected as shown below:

Column 4, line 55, change "[XIII]" to --[VIII]--.

Column 8, line 59, change "1,4-yl-4-benzothiazine)acetic"

to --1,4-benzothiazine-4-yl)acetic--.

Column 14, line 11, change "comopund" to --compound--.

Column 18, TABLE 1, line corresponding to "Compound No.5", right hand column, second line of numeral designations, change "962m" to --962,--.

Column 23, TABLE 4, line corresponding to "Compound No.47", under designation " mp (°C.) ", change "($C_6H_4$)" to --($C_6H_6$)--.

Column 24, TABLE 4, line corresponding to "Compound No.50", under column designation "IR(KBr,$cm^{-1}$)", change numeral designation "144,2" to --1442--.

Column 24, TABLE 4, line corresponding to "Compound No.51"

last line in column designated "IR(KBr,$cm^{-1}$)", change

"1045m" to --1045--.

UNITED STATES PATENT AND TRADEMARK OFFICE
CERTIFICATE OF CORRECTION

PATENT NO. : 4,584,300
DATED : April 22, 1986
INVENTOR(S) : IWAO et al

It is certified that error appears in the above-identified patent and that said Letters Patent is hereby corrected as shown below:

Column 26, TABLE 6, line corresponding to

"Compound No.65$^{*1}$", in column at right-hand side of page, under designation "IR(KBr,cm$^{-1}$)", four lines from bottom of page, change "1510" to --2510--.

Column 28, TABLE 6, line corresponding to "Compound No.66", far right-hand portion of the column, under designation "IR(KBr,cm$^{-1}$)", after numeral designation "1277,", insert --1215,--.

Column 28, TABLE 7, line corresponding to "Compound

No.67*$^1$", under designation "Yield (%)", change "45"

to --35--.

Column 28, TABLE 7, line corresponding to "Compound No.69", right-hand column, under designation "IR(KBr,cm$^{-1}$)", change numerals "1511 1482" to --1513, 1477--.

UNITED STATES PATENT AND TRADEMARK OFFICE
CERTIFICATE OF CORRECTION

PATENT NO. : 4,584,300
DATED : April 22, 1986
INVENTOR(S) : IWAO et al

It is certified that error appears in the above-identified patent and that said Letters Patent is hereby corrected as shown below:

Column 28, TABLE 7, line corresponding to

"Compound No.71*[2]", right-hand column, under designation "IR(KBr,cm$^{-1}$)", second row of numerals, change "1378, 1299, 1240, 748" to

--1475, 1348, 1237, 1022, 754--.

Column 34, TABLE 11, change heading designation

"IRKBr,cm$^{-1}$)" to --IR(KBr,cm$^{-1}$)--.

Column 34, TABLE 11, line corresponding to "Compound No.92", first row of numerals below heading, change "1585m 1499m" to --1585, 1499,--.

Column 34, TABLE 11, line corresponding to "Compound No.92", second row of numerals below heading, change "1241m"

to --1241,--.

Column 34, TABLE 12, last heading designation, change

"IR(KBR,cm$^{-1}$)" to --IR(KBr,cm$^{-1}$)--.

UNITED STATES PATENT AND TRADEMARK OFFICE
CERTIFICATE OF CORRECTION

PATENT NO. : 4,584,300
DATED : April 22, 1986
INVENTOR(S) : IWAO et al It is certified that error appears in the above-identified patent and that said Letters Patent is hereby corrected as shown below:

Column 36, TABLE 12, last heading designation, change

"IR(KBR,cm$^{-1}$)" to --IR(KBr,cm$^{-1}$)--.

Column 40 (Claim 4), line 21, change "claim 1" to

--claim 27--.

Signed and Sealed this

Nineteenth Day of July, 1994

BRUCE LEHMAN

*Attest:*

*Attesting Officer*    *Commissioner of Patents and Trademarks*